US005713950A

United States Patent [19]
Cox

[11] Patent Number: 5,713,950
[45] Date of Patent: Feb. 3, 1998

[54] METHOD OF REPLACING HEART VALVES USING FLEXIBLE TUBES

[76] Inventor: James L. Cox, 7 Dromara Rd., Ladue, Mo. 63124

[21] Appl. No.: 459,979

[22] Filed: Jun. 2, 1995

Related U.S. Application Data

[62] Division of Ser. No. 146,938, Nov. 1, 1993, Pat. No. 5,480,424.

[51] Int. Cl.$^6$ .................................................. A61F 2/24
[52] U.S. Cl. ........................... 623/2; 623/1; 623/66; 623/900; 623/901; 435/238
[58] Field of Search ..................... 623/1, 2, 66, 900, 623/901; 435/238

[56] References Cited

U.S. PATENT DOCUMENTS

| | | | |
|---|---|---|---|
| 3,966,401 | 6/1976 | Hancock et al. | 623/2 |
| 4,108,161 | 8/1978 | Samuels et al. | 206/438 X |
| 4,211,325 | 7/1980 | Wright | 206/438 |
| 4,470,157 | 9/1984 | Love | 623/2 |
| 4,512,471 | 4/1985 | Kaster et al. | 206/438 |
| 4,601,718 | 7/1986 | Possis et al. | 623/1 |
| 4,801,299 | 1/1989 | Brendel et al. | 623/1 |
| 4,838,288 | 6/1989 | Wright et al. | 134/110 |
| 4,960,424 | 10/1990 | Grooters | 623/2 |
| 5,031,762 | 7/1991 | Heacox | 206/210 |
| 5,163,955 | 11/1992 | Love et al. | 623/2 |
| 5,344,442 | 9/1994 | Deac | 623/2 |
| 5,460,962 | 10/1995 | Kemp | 435/238 |
| 5,500,015 | 3/1996 | Deac | 623/2 |

FOREIGN PATENT DOCUMENTS

| | | | |
|---|---|---|---|
| 0276975 | 6/1988 | European Pat. Off. | 623/2 |
| 0581233 | 2/1994 | European Pat. Off. | 623/2 |

OTHER PUBLICATIONS

Wheatley, D., "Valve Prostheses," pp. 415–422 in *Rob & Smith's Operative Surgery*, vol. 7 (Jamieson & Shunway, eds., Mosby–Butterworth, St. Louis, 1986).

Roe, B.B., "Extinct Cardiac Valve Prostheses," pp. 307–332 in *Replacement Cardiac Valves* (Bodnar and Frater, eds., Pergamon Press, New York, 1991).

Love, C.S. and Love, J.W., "The autogenous tissue heart valve: Current Status," *J. Cardiac Surgery* 6: 499–507.

Mickleborough, L.L., et al., "A simplified concept for a bileaflet atrioventricular valve that maintains annular–papillary muscle continuity," *J. Cardiac Surgery* 4: 58–68 (1989).

Bailey, C.P., et al., "Use of autologous tissues in mitral valve reconstruction," *Geriatrics* 25: 119–129 (1970).

David, T.E., et al, "Aortic valve replacement with stentless porcine aortic valve bioprosthesis," *J. Thoracic Cardiovasc. Surg.* 99: 113–118 (1990).

*Primary Examiner*—John G. Weiss
*Assistant Examiner*—Francis K. Cuddihy
*Attorney, Agent, or Firm*—Boyd D. Cox; Patrick D. Kelly

[57] ABSTRACT

This invention comprises a method of using tubular material to replace a heart valve during cardiac surgery. To create a replacement atrioventricular (mitral or tricuspid) valve, the tube inlet is sutured to a valve annulus from which the native leaflets have been removed, and the tube outlet is sutured to papillary muscles in the ventricle. To create a semilunar (aortic or pulmonary) valve, the tube inlet is sutured to an annulus from which the native cusps have been removed, and the tube is either "tacked" at three points distally inside the artery, or sutured longitudinally along three lines; this allows the flaps of tissue between the three fixation points at the valve outlet to function as movable cusps. These approaches generate flow patterns that closely duplicate the flow patterns of native valves. One preferred tubular material comprises submucosal tissue from a small intestine, from the same patient who is undergoing the cardiac operation; this eliminates the risk of immune rejection and the need to treat the tissue to reduce antigenicity. Intestinal tissue from human cadavers or animals such as genetically engineered hypoallergenic pigs can also be used, if properly treated, or a biocompatible synthetic tubular material can be used.

10 Claims, 4 Drawing Sheets

METHOD OF REPLACING HEART VALVES USING FLEXIBLE TUBES

RELATED APPLICATION

This is a divisional application, based on prior U.S. application Ser. No. 08/146,938, filed on Nov. 1, 1993, issued on Jan. 2, 1996 U.S. Pat. No. 5,480,424.

BACKGROUND OF THE INVENTION

This invention is in the field of heart surgery and relates to replacement of diseased or injured heart valves.

Anatomy of Normal Heart Valves

There are four valves in the heart that serve to direct the flow of blood through the two sides of the heart in a forward direction. On the left (systemic) side of the heart are: 1) the mitral valve, located between the left atrium and the left ventricle, and 2) the aortic valve, located between the left ventricle and the aorta. These two valves direct oxygenated blood coming from the lungs, through the left side of the heart, into the aorta for distribution to the body. On the right (pulmonary) side of the heart are: 1) the tricuspid valve, located between the right atrium and the right ventricle, and 2) the pulmonary valve, located between the right ventricle and the pulmonary artery. These two valves direct de-oxygenated blood coming from the body, through the right side of the heart, into the pulmonary artery for distribution to the lungs, where it again becomes re-oxygenated to begin the circuit anew.

All four of these heart valves are passive structures in that they do not themselves expend any energy and do not perform any active contractile function. They consist of moveable "leaflets" that are designed simply to open and close in response to differential pressures on either side of the valve. The mitral and tricuspid valves are referred to as "atrioventricular valves" because of their being situated between an atrium and ventricle on each side of the heart. The mitral valve has two leaflets and the tricuspid valve has three. The aortic and pulmonary valves are referred to as "semilunar valves" because of the unique appearance of their leaflets, which are more aptly termed "cusps" and are shaped somewhat like a half-moon. The aortic and pulmonary valves each have three cusps.

Since the physiological structures of native mitral and tricuspid valves and native aortic and pulmonary valves are important to this invention, they are depicted in FIG. 1, which contains a cross-sectional cutaway depiction of a normal human heart 100 (shown next to heart 100 is a segment of tubular tissue 200 which will be used to replace the mitral valve, as described below). The left side of heart 100 contains left atrium 110, left ventricular chamber 112 positioned between left ventricular wall 114 and septum 116, aortic valve 118, and mitral valve assembly 120. The components of the mitral valve assembly 120 include the mitral valve annulus 121, which will remain as a roughly circular open ring after the leaflets of a diseased or damaged valve have been removed; anterior leaflet 122 (sometimes called the aortic leaflet, since it is adjacent to the aortic region); posterior leaflet 124; two papillary muscles 126 and 128 which are attached at their bases to the interior surface of the left ventricular wall 114; and multiple chordae tendineae 132, which couple the mitral valve leaflets 122 and 124 to the papillary muscles 126 and 128. There is no one-to-one chordal connection between the leaflets and the papillary muscles; instead, numerous chordae are present, and chordae from each papillary muscle 126 and 128 attach to both of the valve leaflets 122 and 124.

The other side of the heart contains the right atrium 150, a right ventricular chamber 152 bounded by right ventricular wall 154 and septum 116, and a tricuspid valve assembly 160. The tricuspid valve assembly 160 comprises a valve annulus 162, three leaflets 164, papillary muscles 170 attached to the interior surface of the right ventricular wall 154, and multiple chordae tendineae 180 which couple the tricuspid valve leaflets 164 to the papillary muscles 170–174.

As mentioned above, the mitral valve leaflets 122 and 124, and tricuspid valve leaflets 164 are all passive structures; they do not themselves expend any energy and do not perform any active contractile function. They are designed to simply open and close in response to differential pressures on either side of the leaflet tissue. When the left ventricular wall 114 relaxes so that the ventricular chamber 112 enlarges and draws in blood, the mitral valve 120 opens (i.e., the leaflets 122 and 124 separate). Oxygenated blood flows in a downward direction through the valve 120, to fill the expanding ventricular cavity. Once the left ventricular cavity has filled, the left ventricle contracts, causing a rapid rise in the left ventricular cavitary pressure. This causes the mitral valve 120 to close (i.e., the leaflets 122 and 124 re-approximate) while the aortic valve 118 opens, allowing the oxygenated blood to be ejected from the left ventricle into the aorta. The chordae tendineae 132 of the mitral valve prevent the mitral leaflets 122 and 124 from prolapsing back into the left atrium 110 when the left ventricular chamber 114 contracts.

The three leaflets, chordae tendineae, and papillary muscles of the tricuspid valve function in a similar manner, in response to the filling of the right ventricle and its subsequent contraction.

The cusps of the aortic valve also respond passively to pressure differentials between the left ventricle and the aorta. When the left ventricle contracts, the aortic valve cusps open to allow the flow of oxygenated blood from the left ventricle into the aorta. When the left ventricle relaxes, the aortic valve cusps reapproximate to prevent the blood which has entered the aorta from leaking (regurgitating) back into the left ventricle. The pulmonary valve cusps respond passively in the same manner in response to relaxation and contraction of the right ventricle in moving de-oxygenated blood into the pulmonary artery and thence to the lungs for re-oxygenation. Neither of these semilunar valves has associated chordae tendineae or papillary muscles.

In summary, with relaxation and expansion of the ventricles (diastole), the mitral and tricuspid valves open, while the aortic and pulmonary valves close. When the ventricles contract (systole), the mitral and tricuspid valves close and the aortic and pulmonary valves open. In this manner, blood is propelled through both sides of the heart.

The anatomy of the heart and the structure and terminology of heart valves are described and illustrated in detail in numerous reference works on anatomy and cardiac surgery, including standard texts such as *Surgery of the Chest* (Sabiston and Spencer, eds., Saunders Publ., Philadelphia) and *Cardiac Surgery* by Kirklin and Barrett-Boyes.

Pathology and Abnormalities of Heart Valves

Heart valves may exhibit abnormal anatomy and function as a result of congenital or acquired valve disease. Congenital valve abnormalities may be so severe that emergency surgery is required within the first few hours of life, or they may be well-tolerated for many years only to develop a life-threatening problem in an elderly patient. Acquired valve disease may result from causes such as rheumatic fever, degenerative disorders of the valve tissue, bacterial or fungal infections, and trauma.

Since heart valves are passive structures that simply open and close in response to differential pressures on either side of the particular valve, the problems that can develop with valves can be classified into two categories: 1) stenosis, in which a valve does not open properly, or 2) insufficiency (also called regurgitation), in which a valve does not close properly. Stenosis and insufficiency may occur concomitantly in the same valve or in different valves. Both of these abnormalities increase the workload placed on the heart, and the severity of this increased stress on the heart and the patient, and the heart's ability to adapt to it, determine whether the abnormal valve will have to be surgically replaced (or, in some cases, repaired) or not.

In addition to stenosis and insufficiency of heart valves, surgery may also be required for certain types of bacterial or fungal infections in which the valve may continue to function normally, but nevertheless harbors an overgrowth of bacteria (a so-called "vegetation") on the leaflets of the valve that may flake off ("embolize") and lodge downstream in a vital artery. If such vegetations are on the valves of the left side (i.e., the systemic circulation side) of the heart, embolization results in sudden loss of the blood supply to the affected body organ and immediate malfunction of that organ. The organ most commonly affected by such embolization is the brain, in which case the patient suffers a stroke. Thus, surgical replacement of either the mitral or aortic valve (left-sided heart valves) may be necessary for this problem even though neither stenosis nor insufficiency of either valve is present. Likewise, bacterial or fungal vegetations on the tricuspid valve may embolize to the lungs (resulting in a lung abscess) and therefore, may require replacement of the tricuspid valve even though no tricuspid valve stenosis or insufficiency is present. With the exception of congenital pulmonary valve stenosis or insufficiency, it is unusual for a patient to develop an abnormality of the pulmonary valve that is significant enough to require surgical repair or replacement.

Currently, surgical repair of mitral and tricuspid valves is preferred over total valve replacement when possible, although often the valves are too diseased to repair and must be replaced. Most abnormalities of the aortic valve require replacement, although some efforts are now being made to repair insufficient aortic valves in selected patients. Valve repair and valve replacement surgery is described and illustrated in numerous books and articles, including the texts cited herein.

CURRENT OPTIONS FOR HEART VALVE REPLACEMENT

If a heart valve must be replaced, there are currently several options available, and the choice of a particular type of prosthesis (i.e., artificial valve) depends on factors such as the location of the valve, the age and other specifics of the patient, and the surgeon's experiences and preferences. Available prostheses include three categories of valves or materials: mechanical valves, tissue valves, and aortic homograft valves. These are briefly discussed below; they are illustrated and described in detail in texts such as *Replacement Cardiac Valves*, edited by E. Bodnar and R. Frater (Pergamon Press, New York, 1991).

Artificial Mechanical Valves

Mechanical valves include caged-ball valves (such as Starr-Edwards valves), bi-leaflet valves (such as St. Jude valves), and tilting disk valves (such as Medtronic-Hall or Omniscience valves). Caged ball valves usually are made with a ball made of a silicone rubber (Silastic™) inside a titanium cage, while bi-leaflet and tilting disk valves are made of various combinations of pyrolytic carbon and titanium. All of these valves are attached to a cloth (usually Dacron™) sewing ring so that the valve prosthesis can be sutured to the patient's native tissue to hold the artificial valve in place postoperatively. All of these mechanical valves can be used to replace any of the heart's four valves. No other mechanical valves are currently approved for use by the FDA in the U.S.A.

The main advantage of mechanical valves is their long-term durability. Their main disadvantage is that they require the patient to take systemic anticoagulation drugs for the rest of his or her life, because of the propensity of mechanical valves to cause blood clots to form on them. If such blood clots form on the valve, they may preclude the valve from opening or closing correctly or, more importantly, the blood clots may disengage from the valve and embolize to the brain, causing a stroke. The anticoagulant drugs that are necessary to prevent this are expensive and potentially dangerous in that they may cause abnormal bleeding which, in itself, can cause a stroke if the bleeding occurs within the brain.

In addition to the mechanical valves available for implantation today, a number of other valve designs are described and illustrated in a chapter called "Extinct Cardiac Valve Prostheses," at pages 307–332 of *Replacement Cardiac Valves* (Bodnar and Frater, cited above). Two of the "extinct" valves which deserve attention as prior art in the subject invention are the McGoon valve (pp. 319–320) and the Roe-Moore valve (pp. 320–321). Both of these involve flexible leaflets made of an elastomer or cloth coated with polytetrafluoroethylene (PTFE, widely sold under the trademark TEFLON), mounted inside a cylindrical stent. Although both were tested in humans, they were never commercialized and apparently are not being actively studied or developed today.

Artificial Tissue Valves

Most tissue valves are constructed by sewing the leaflets of pig aortic valves to a stent (to hold the leaflets in proper position), or by constructing valve leaflets from the pericardial sac (which surrounds the heart) of cows or pigs and sewing them to a stent. The stents may be rigid or slightly flexible and are covered with cloth (usually a synthetic material sold under the trademark Dacron™) and attached to a sewing ring for fixation to the patient's native tissue. The porcine or bovine tissue is chemically treated to alleviate any antigenicity (i.e., to reduce the risk that the patient's body will reject the foreign tissue). These tri-leaflet valves may be used to replace any of the heart's four valves. The only tissue valves currently approved by the FDA for implantation in the U.S.A. are the Carpentier-Edwards Porcine Valve, the Hancock Porcine Valve, and the Carpentier-Edwards Pericardial Valve.

The main advantage of tissue valves is that they do not cause blood clots to form as readily as do the mechanical valves, and therefore, they do not absolutely require systemic anticoagulation. Nevertheless, many surgeons do anticoagulate patients who have any type of artificial mitral valve, including tissue valves. The major disadvantage of tissue valves is that they lack the long-term durability of mechanical valves. Tissue valves have a significant failure rate, usually appearing at approximately 8 years following implantation, although preliminary results with the new commercial pericardial valves suggest that they may last longer. One cause of these failures is believed to be the chemical treatment of the animal tissue that prevents it from being antigenic to the patient. In addition, the presence of the stent and sewing ring prevents the artificial tissue valve from being anatomically accurate in comparison to a normal heart valve, even in the aortic valve position.

Homograft Valves

Homograft valves are harvested from human cadavers. They are most commonly aortic valves but also occasionally include pulmonic valves. These valves are specially prepared and frozen in liquid nitrogen, where they are stored for later use in adults for aortic valve replacement, or in children for pulmonary valve replacement. A variant occasionally employed for aortic valve replacement is to use the patient's own pulmonary valve (an autograft) to replace a diseased aortic valve, combined with insertion of an aortic (or pulmonary) homograft from a cadaver to replace the excised pulmonary valve (this is commonly called a "Ross procedure").

The advantage of aortic homograft valves is that they appear to be as durable as mechanical valves and yet they do not promote blood clot formation and therefore, do not require anticoagulation. The main disadvantage of these valves is that they are not available in sufficient numbers to satisfy the needs of patients who need new aortic or pulmonary valves. They also cannot be used to replace either the mitral valve or tricuspid valve. In addition, they are extremely expensive and much more difficult to implant than either mechanical or tissue valves. The difficulty in implantation means that the operative risk with a homograft valve is greater in a given patient than it is with either a mechanical or tissue valve. An additional problem is that in June 1992, the FDA re-classified homograft valves as an experimental device, so they are no longer available on a routine basis.

PRINCIPLES OF ARTIFICIAL HEART VALVE CONSTRUCTION

All artificial heart valves are designed to optimize three major physiologic characteristics and one practical consideration. The three major physiologic characteristics are (1) hemodynamic performance, (2) thrombogenicity, and (3) durability. The practical consideration involves ease of surgical implantation.

Multiple factors impact on each of these potential problems in the development of artificial valves. As a result, the advantage of artificial valve A over artificial valve B in one area is typically counterbalanced by valve B's advantage in another area. If one artificial heart valve were clearly superior in all aspects to all other artificial valves in all four of these areas, it would be the only artificial valve used.

Artificial Mechanical Valves

The hemodynamic performance of mechanical heart valves has been satisfactory but not optimal, especially in the smaller sizes. All previously constructed mechanical heart valves have had some type of obstructing structure within the flow orifice of the valve when the valve is in the open position. For example, bi-leaflet valves, such as the St. Jude valve, have two bars across the orifice and in addition, the leaflets themselves are within the orifice when the valve is in the open position. Single-leaflet disc valves, such as the Medtronic-Hall valve, have a central bar and strut mechanism that keep the leaflet in place. The Bjork-Shiley valves have either one or two struts that span the valve orifice in addition to the partially-opened disc itself. The Omniscience valve has the partially opened disk itself in the valve orifice when open, and the Starr-Edwards caged-ball valve has both the ball and the cage within the flow orifice of the valve in the open position. All of these structures decrease the hemodynamic performance of the mechanical valves.

Such obstructions also interfere with the normal flow patterns within and around the mechanical valve and therefore, promote thrombosis. More importantly, all artificial surfaces are thrombogenic (clot-promoting) to a greater or lesser degree. The only completely non-thrombogenic (non-clot-promoting) surface that exists is the layer of viable endothelial cells that line the interior of all the body's vascular surfaces, including the inside of the heart chambers and the native valve leaflets. Therefore, any metal or plastic material, no matter how highly polished, will have some level of thrombogenicity unless the surface of the artificial material can be covered with endothelial cells. It is for this reason that all patients with artificial mechanical heart valves must be permanently anticoagulated.

The major advantage of mechanical valves over tissue valves is long-term durability. Mechanical valve construction has been based on sophisticated engineering principles that have proven to be sound in terms of providing devices that are extremely resistant to wear and structural failure. Nevertheless, structural failure of mechanical valves does occur and it is the major reason for the recent withdrawal from the market of two commercially available mechanical valves (the Bjork-Shiley Concavo-Convex™ single disc valve and the Duramedics™ bi-leaflet valve).

Artificial Tissue Valves

Under the best of circumstances (i.e., replacement of the aortic valve), the construction of artificial tissue valves has been based on the concept that if the artificial valve can be made to approximate the anatomy (form) of the native valve, then the physiology (function) of the artificial valve will also approximate that of the native valve. This is the concept that "Function Follows Form." For example, the manufacturers of all artificial porcine valves first re-create the form of a native human aortic valve by: 1) harvesting a porcine aortic valve, 2) fixing it in glutaraldehyde to eliminate antigenicity, and 3) suturing the porcine valve to a stent to hold the three leaflets in place. In other words, the primary goal in the construction of these artificial valves is to reproduce the form of the human aortic valve as closely as possible. The assumption is made that if the artificial valve can be made to look like the human aortic valve, it will function like the human aortic valve (i.e., proper function will follow proper form). The same assumption is also followed for commercially available pericardial valves.

In the case of mitral or tricuspid valve replacement, even the dubious concept of "function follows form" has been discarded since the same artificial valves that are designed to look like the aortic valve are used to replace the mitral and tricuspid valves. In other words, no attempt at all is made to reproduce even the form of these native valves, much less so their function.

Thus, in the case of artificial valves to be used for aortic valve replacement, the dubious concept of "function follows form" has dictated the construction of all artificial tissue valves during the 30 years of their development and use. Even worse, no discernable underlying concept at all has been used in terms of the artificial valves used to replace the mitral and tricuspid valves.

The "Function Follows Form" concept has several limitations and appears to be a fundamental shortcoming which underlies the present construction of all artificial tissue valves. In the first place, it simply is not possible to re-create the exact anatomy (form) of a native heart valve utilizing present techniques. Although homograft (human cadaver) and porcine aortic valves have the gross appearance of native aortic valves, the fixation process (freezing with liquid nitrogen, and chemical treatment, respectively) alters the histologic (microscopic) characteristics of the valve tissue. Porcine and bovine pericardial valves not only require chemical preparation (usually involving fixation with glutaraldehyde), but the leaflets must be sutured to cloth-covered stents in order to hold the leaflets in position for proper opening and closing of the valve. A recent advance has been made in this regard by using "stentless" porcine valves that are sutured directly to the patient's native tissues for aortic valve replacement, but the problem of chemical fixation remains. In addition, these stentless artificial valves cannot be used for mitral or tricuspid valve replacement.

Perhaps the major limitation of the "Function Follows Form" concept is that no efforts have been made previously to approximate the form of either the mitral valve or the tricuspid valve. If animal tissue valves are used to replace either of these native valves, the tri-leaflet porcine aortic valve prosthesis or the tri-leaflet bovine pericardial valve prosthesis is normally used. In doing so, even the faulty concept of "Function Follows Form" is ignored, since there are no artificial valves available for human use that approximate the anatomy (form) of the native mitral or tricuspid valves.

The nearest attempt at reproducing the function of the native mitral valve was reported by Mickleborough et al in 1989. These tests involved the use of commercially-prepared sheets of pericardial tissue from cows, which had been treated with glutaraldehyde before storage and shipping. A longitudinal suture line was used to convert the flat sheet of tissue into a cylinder, then two triangular regions were removed from one end of the cylinder, to generate two flaps. The inlet end was sutured to the mitral valve annulus, while the two tissue flaps at the carved outlet end were sutured to the papillary muscles.

The mitral valve disclosed by Mickleborough et al suffers from a drawback which is believed to be important and perhaps even crucial to proper valve functioning. In a properly functioning natural valve, the anterior leaflet does not have its center portion directly attached to the anterior papillary muscle via chordae. Instead, the anterior leaflet is attached to both the anterior and posterior papillary muscles, via chordae that are predominantly attached to the peripheral edges of the leaflet. In the same manner, a native posterior leaflet is attached to both the anterior and posterior papillary muscles, via chordae that are predominantly attached to the peripheral edges of the leaflet. As a result, the line of commissure (closure) between the two mitral leaflets when the valve is closed during systole is oriented in roughly the same direction as an imaginary line that crosses the tips of both papillary muscles. This orientation of the leaflets and papillary muscles is shown in illustrations such as page 11 of Netter 1969. This natural orientation can be achieved in the valve of the subject invention as depicted in FIGS. 2 and 3, discussed below.

By contrast, the replacement valve described by Mickleborough et al alters and distorts the proper orientation of the replacement leaflets. Mickleborough's approach requires each sculpted leaflet to be trimmed in a way that forms an extended flap, which becomes a relatively narrow strand of tissue near its tip. The tip of each pericardial tissue strand is sutured directly to a papillary muscle, causing the strand to mimic a chordae tendineae. Each strand extends from the center of a leaflet in the Mickleborough et al valve, and each strand is sutured directly to either an anterior and posterior papillary muscle. This requires each leaflet to be positioned directly over a papillary muscle. This effectively rotates the leaflets of the Mickleborough valve about 90° compared to the leaflets of a native valve. The line of commissure between the leaflets, when they are pressed together during systole, will bisect (at a perpendicular angle) an imaginary line that crosses the peaks of the two papillary muscles, instead of lying roughly along that line as occurs in a native valve.

There has been no indication since the publication of Mickleborough et al 1989 that their approach is still being studied (either by them, or by any other research team), and there has been no other indication during the intervening years that their approach is likely to lead to a valve replacement technique for actual use in humans.

It should be noted that one of the primary goals of Mickleborough and her associates apparently was to propose a new way to maintain continuity between the valve annulus and the papillary muscles. It was first proposed about 30 years ago (by C. W. Lillehei and perhaps by others as well) that proper muscle tone of the left ventricular wall, and proper postoperative ventricular functioning, required a tension-bearing connection between the mitral valve annulus and the papillary muscles on the inside of the ventricular wall. This suggestion was widely ignored in the design of replacement mitral valves, which required excision of the chordae tendineae without making any effort to provide a substitute that would keep the ventricular wall coupled to the valve annulus. However, various studies (such as Rittenhouse et al 1978, David 1986, Hansen et al 1987, and Miki et al 1988) continued to indicate that the tension-conveying role of the chordae was important to proper ventricular function. Based on those studies, Mickleborough et al apparently were attempting to create and propose a new valve design that could accomplish that goal. They did indeed accomplish that goal, and the apparent lack of any followup or commercialization of their design presumably was due to other problems, such as the altered orientation of the leaflets in their design.

A different approach to creating artificial tissue valves is described in articles such as Love and Love 1991, and in U.S. Pat. Nos. 5,163,955 (Calvin et al 1992) and 4,470,157 (Love 1984). In that research, surgeons harvested a piece of pericardial tissue from the same animal that was to receive the artificial valve. Such tissue, if harvested from the same human body that will receive the implant, is referred to as autologous or autogenous (the terms are used interchangeably, by different researchers). Using a cutting die, the pericardial tissue was cut into a carefully defined geometric shape, treated with glutaraldehyde, then clamped in a sandwich-fashion between two stent components. This created a tri-leaflet valve that again resembles an aortic or pulmonary valve, having semilunar-type cusps rather than atrioventricular-type leaflets. These valves were then tested in the mitral (or occasionally tricuspid) valve position, using sheep.

Although those valves were structurally very different from the valves of the subject invention, the Love and Love article is worth attention because it discusses chemical fixation. They used glutaraldehyde treatment even though their tissue source was from the same animal and was therefore non-antigenic, because earlier reports and tests had suggested that some types of untreated autologous tissue suffer from thickening and/or shrinkage over time. Love and Love suggested that glutaraldehyde can help such tissue resist such changes, apparently by forming crosslinking bonds that tend to hold adjacent collagen fibers in a fixed-but-flexible conformation. This use of glutaraldehyde fixation as a treatment to reduce shrinkage or other physical distortion (as distinct from using it as a method of reducing tissue antigenicity) is an old and well-established technique for treating non-autologous tissue, but whether it is also beneficial for treating autologous tissue has not yet been extensively evaluated. The effects of chemical fixation of intestinal or other tubular tissue used to create heart valves as described herein can be evaluated by routine experimentation.

Another report describing the use of autologous tissue to reconstruct mitral valves is Bailey et al 1970. However, Bailey et al focused on repairing rather than replacing mitral valves, usually by cutting an incision into one or both leaflets and then inserting a segment of tissue into the incision to enlarge the leaflet(s).

PHYSIOLOGIC FACTORS AND IN UTERO DEVELOPMENT

The subject invention relates to a method of using tubular starting material to replace any of the four heart valves during cardiac surgery. This approach is supported by and consistent with a fundamental principle of native heart valve function, which either went unrecognized in previous efforts to develop replacement valves, or which was sacrificed and lost when compromises were required to adapt available materials to surgical requirements.

The basic principle, which deserves repeated emphasis because it has been so widely disregarded by other efforts in this field, is that Form Follows Function. In one manifestation of this principle, if an artificial valve can be created that can truly function like a native valve, its resultant form will be similar to that of the native valve.

A highly important observation by the Applicant that contributed to the recognition of the pervasive and overriding importance of this principle was the following: the entire cardiovascular system, including the heart, begins in utero as a single, relatively straight tube of tissue. Anatomical drawings depicting the in utero development of the heart are available in numerous scientific publications and books, including Netter 1969. As shown in those figures (or similar figures available in other medical reference works), the so-called "heart tube" is readily discernible by the 23rd day of gestation. This tube will eventually develop into the entire cardiovascular system of the body. The tissue that exists between the portion of the tube destined to become the ventricles, and the portion that will become the atria, is where the mitral and tricuspid valves will ultimately form. This region of tissue is in a tubular form.

The heart tube undergoes a process of convolution beginning at approximately 25 days gestation. This convolution of the heart tube forms what is called the "heart loop" and is responsible for the aortic valve ultimately coming to lie adjacent to the mitral valve. When a mature mitral valve is viewed from the atrial side, the anterior portion of the mitral valve annulus is relatively flat. This distortion of the original roundness of the mitral annulus is caused by the presence of the aorta against the anterior mitral valve. It is also the reason that the anterior leaflet of the mitral valve is contiguous with the aortic valve annulus. Finally, it explains why accessory atrioventricular connections (accessory pathways) that occur in the Wolff-Parkinson-White syndrome never occur in this portion of the mitral valve annulus; this is the only portion of the entire atrioventricular groove on either side of the heart where the atrium and ventricle were never contiguous during fetal development.

By approximately 56 days gestation, the heart tube development reaches a stage that displays a first constricted tube region between the primordial right atrium and the primordial right ventricle (this portion of the tube will become the tricuspid valve) and a second constricted tube region between the primordial left atrium and primordial left ventricle (the future mitral valve).

As the developing heart of a fetus undergoes various convolutions, septations, and compartmentalizations, the tissues that are to eventually become the heart valves maintain their tubular structure. Prior to the onset of fetal heart function, portions of the walls of these tubular structures undergo a process of dissolution, leaving behind only those portions of the original tubes that are necessary for the proper functioning of the heart. This dissolution also affects the ventricular walls as they rapidly enlarge in size; if it did not, the walls would become prohibitively thick as the physical size of the heart increased, and the heart could not function effectively as a pump since it would become simply a large mass of ventricular muscle.

The dissolution process also operates on the tubular constrictions that will become the four heart valves. In the case of the semilunar valves (the aortic and pulmonary valves), the necessary functional remnants are the three cusps, which are the remains of the functioning portion of a simple tube. This principle is strengthened by the fact that although frequent reference is made to the pulmonic or aortic valve "annulus", knowledgeable anatomists are quick to point out that there is no such anatomical structure. The thickened tissue that is commonly referred to as the "annulus" of these valves is simply the flexion point of the three cusps, the remnants of a simple tube that is fixed at three points distally and subjected to uniform pressure on its outside, resulting in collapse of the tube on the three sides between the points of distal fixation, which in turn, results in three nearly identical cusps. All tissue other than these moveable and functional cusps has undergone the normal process of dissolution as the aorta and pulmonary artery have enlarged, leaving behind only that tissue recognized as the cusps of these semilunar valves.

At the mitral and tricuspid valves locations, the dissolution process leaves behind the valve leaflets, chordae tendineae, and papillary muscles in both the right ventricle (tricuspid valve) and left ventricle (mitral valve). In other words, that portion of the original tube that is necessary for the development of the native heart valves is spared the dissolution process and the rest of the tube dissolves away. The valve leaflets are tube remnants, which are attached circumferentially to the fibrous annulus of the heart at their base and attached by chordae tendineae (additional tube remnants) at their free edges to papillary muscles (still more tube remnants) inside the ventricles. The leaflets, chordae tendineae, and papillary muscles of each the two A--V valves represent the necessary functional remnants of the original in utero tubular structures of the heart.

Using "Form Follows Function" as a basic guiding principle, the present invention is based on the realization that a tubular structure having proper size and suitable material characteristics, if placed inside a mitral or tricuspid valve annulus after excision of the native valve (or inside an aorta or pulmonary artery, as described below) will function exactly like the normal valve in that position, assuming proper fixation of the inlet and outlet ends of the tube. The "Form Follows Function" principle predicts that if the intended function of a replacement valve is to emulate the performance and function of a native mitral or tricuspid valve, then the form of a replacement valve----the structure and appearance of the replacement valve----should resemble the form of a native mitral or tricuspid valve. Since the native valves are generated from tubular starting material during fetal development, this principle further suggests that replacement valves should also be generated from tubular material.

This principle is given added support by the results that were observed in an artificial tissue valve that had been implanted into the mitral valve position in a human heart. The Applicant learned of these results during a presentation by Professor Donald Ross of the National Heart Hospital and Brompton Hospital (London, England), the cardiac surgeon who had performed that surgery. The implanted valve was originally a commercially available trileaflet tissue valve that was implanted into the mitral position in a 35-year-old female. The trileaflet valve had been constructed using fascia lata tissue (a relatively tough and flexible layer of tissue that normally surrounds certain types of muscles) which had been sewn into a circular stent. After 5 years, the artificial valve had to be removed because its leaflets had become calcified and immobile, resulting in both mitral stenosis and mitral insufficiency. Upon exposing the artificial valve during the removal surgery, the surgeon was struck by the similarity in shape and appearance of the diseased trileaflet valve to a normal mitral valve. The commissures of the three leaflet artificial tissue valve had fused in a manner so that two leaflets had been formed: one large anterior leaflet, and one smaller posterior leaflet, as seen in a native mitral valve. Furthermore, the commissure between the two leaflets when the patent's valve was closed by back pressure closely resembled the semi-circular commissure formed by leaflets in a native mitral valve.

During the presentation by Professor Ross, the Applicant witnessed a picture showing how the three-leaflet artificial valve had been converted into a bi-leaflet valve during the course of five years inside a human heart. It became clear to the Applicant that the patient's heart had been attempting to make the valve conform to the heart's functional needs.

Prior to witnessing that presentation, the Applicant had already been considering the question of whether tubular tissue might be useful for creating replacement heart valves. After seeing Prof. Ross's photographs, which provided strong physiological confirmation of the "Form Follows Function" principle, the Applicant began to carry out experiments to assess the possibility of using tubular tissue to replace heart valves. In a simple mechanical test, he obtained some highly flexible rubber tubes by cutting off the fingers of surgical gloves, then he sculpted the finger tubes to resemble the leaflets of mitral or tricuspid valves, then he sutured the sculpted rubber tubes inside of slightly larger tubes made of Dacron™. An internal rubber tube was secured proximally around the entire periphery of a tube, to emulate a valve annulus, and the sculpted rubber flaps at the distal ends were coupled to the tube walls by means of loose suture strands that emulated chordae tendineae. When cyclical pressure was generated by attempting to blow and then suck air through the tube, the interior rubber leaflets opened and closed in a manner that looked identical to natural mitral or tricuspid leaflets opening and closing. This provided additional confirmation of the "Form Follows Function" principle.

The physiologic principle that the functional components of native heart valves are the remnants of simple tissue tubes, and the idea of using tubular structures to replace defective heart valves, has been completely ignored in the design and construction of all replacement valves in use today. Indeed, although "Form Follows Function" is a well-respected principle in fields such as engineering or evolutionary studies, it is often disregarded among medical researchers, some of whom apparently seem to feel that efforts to sever or reverse this relationship represent triumphs of technology over nature. As an example, kidney dialysis machines, which look nothing like normal kidneys, are a purely technological, non-natural solution; they use a completely artificial form to generate and provide a certain needed function. However, as any dialysis patient would attest, they fall far short of being truly optimal.

In a similar manner, all artificial heart valves in use today, whether tissue or mechanical, have been designed based on the belief that either: 1) function can be forced to follow form (aortic and pulmonary valve replacement), or 2) neither function nor form of the native valve can be reproduced, so a replacement valve (either tissue or mechanical) must merely function as a one-way passive valve (mitral and tricuspid valve replacement). In the case of artificial tissue valves, the form of an artificial valve is established first, in the hope that the valve will function in a manner similar to a native valve. In the case of artificial mechanical valves, the disruption of the interaction between form and function goes even farther, and the caged balls, hinged flappers, and other devices in mechanical valves have even less physical similarity to native valves. However, the problems in both of these approaches are evident in the limitations suffered by every type of replacement valve that is in use today.

There is another way to express the concept of "Form Follows Function" which may help explain it to people who would point to mechanical heart valves, dialysis machines, and other non-natural forms that have been used to mimic the function of body parts. In such examples, function is forced to follow form. In crude and simple terms, the function of a heart valve is merely to allow flow in one direction only. Any type of mechanical check valve with a caged-ball or flapper-and-seat design can provide that level of function.

However, when the long-term aspects of heart valve function are also taken into account (including the functions of providing low hemolysis, low turbulence, avoiding calcification, etc.), it becomes clear that artificial forms cannot fully provide those functions. The best and perhaps only way to provide a replacement valve with the complete, long-term functionality of a natural heart valve is by giving proper deference to the relationship between function and form.

This principle can be stated as, "Form and function form a cycle." Each follows the other, but each also precedes and affects the other. If either half of this cycle is violated or disrupted, it will create problems that will stand in the way of an optimally functional, reliable, durable system with minimal hemolysis, turbulence, and calcification. On a short-term basis, function can be forced to adapt to an unnatural form; however, any such short-term solution will be plagued by problems and limitations over the long run. The problems and shortcomings of current mechanical replacement valves are a clear and direct demonstration of this principle.

The following series can help to illustrate the principle, "Form and function form a cycle." First, a form is created: tubular tissue is used to create a new mitral valve. This form then creates a function: the new valve allows flow in only one direction, from the atrium to the ventricle. This function, in turn, creates another form: the leaflets of the new mitral valve will close in a "smile" configuration resembling a native mitral valve during closure. This secondary form then creates a secondary function: the new valve will provide good long-term use and low levels of turbulence, hemolysis, calcification, and leaflet stress. Form and function form a cycle, and this cycle cannot be disrupted by injecting and imposing an artificial, unnatural form in the heart without impeding the ability of proper form and proper function to interact with, support, and enhance each other.

In addition, certain items of evidence suggest that conventional replacement tissue valves, which cause high levels of turbulence, contribute to the important problem of leaflet calcification. The correlation between high turbulence and leaflet calcification is discussed below.

Objects of the Invention

On the basis of the physiological facts, observations, and principles described above, and on the basis of experiments carried out by the Applicant, it appears that if heart valves are damaged or diseased to the point of requiring replacement, they should be replaced by tubular structures which function like native heart valves.

Accordingly, one object of this invention is to provide a method of surgically replacing heart valves using natural autologous tubular tissue (i.e., the patient's own tissue) as the starting material. Use of the patient's own tissue can completely avoid the need for chemical processing, freezing, or other treatment, which are required to reduce the antigenicity of tissue obtained from animals or cadavers.

Another object of this invention is to provide a method of surgically replacing heart valves using innately tubular material (i.e., tissue or synthetic material which is harvested or synthesized in tubular form) as the starting material, to increase the long-term durability of replacement heart valves.

Another object of this invention is to provide a method of using tubular starting material to create a replacement heart valve without requiring the use of a foreign object such as a stent to secure the replacement valve in position.

Another object of this invention is to provide a method of using tissue from a patient's own small intestine to create a replacement heart valve.

Another object of this invention is to provide replacement valves which are covered by a layer of epithelial cells, which do not create a risk of blood clot formation, thereby eliminating the need for a patient to take anti-coagulant drugs for the rest of his or her life.

These and other objects and advantages of the invention will become clear as the invention and certain preferred embodiments are described below and in the drawings.

SUMMARY OF THE INVENTION

This invention comprises a method of using tubular material to replace a heart valve during cardiac surgery. To create a replacement mitral or tricuspid valve, the tube inlet is sutured to the mitral or tricuspid valve annulus, and the outlet end of the tube is sutured to papillary muscles in the ventricle. To create an aortic or pulmonary valve, the tube inlet is sutured to the aortic or pulmonary valve annulus, and the tube is either "tacked" at three points distally, or sutured longitudinally along three lines; either method will allow the flaps of tissue between the suture lines to function as movable cusps. These approaches generate flow patterns that closely duplicate the flow patterns of the native valves.

A preferred non-antigenic material comprises a segment of submucosal tissue from the small intestine of the same patient who is undergoing the cardiac operation. By using tissue from the same patient, the risk of immune rejection and the need to use fixation treatment to reduce the antigenicity of animal or cadaver tissue are eliminated. Alternately, animal or human cadaver intestinal tissue can be used if desired, if properly treated (such as by glutaraldehyde fixation) to reduce antigenicity, or biocompatible synthetic materials can be used.

This invention also discloses a prepared, chemically treated intestinal tissue segment suitable for implantation as a replacement heart valve, with or without an annuloplasty ring attached to the tissue segment, enclosed in a sealed sterile package.

DESCRIPTION OF THE PREFERRED EMBODIMENTS

Figure 1:
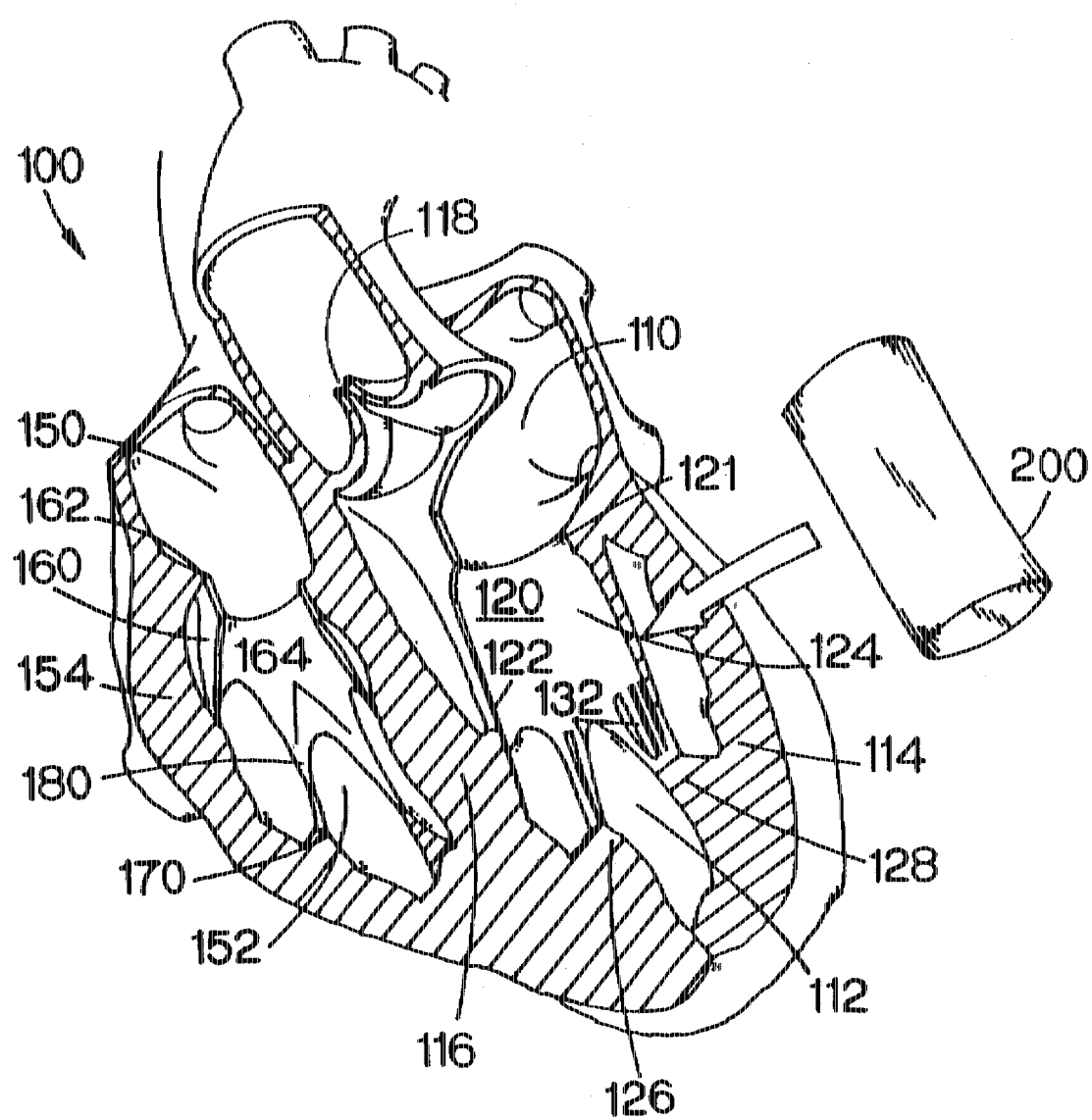
FIG. 1 is a cutaway depiction showing the mitral valve on the left (systemic) side of the heart and the tricuspid valve on the right (pulmonary) side of the heart, showing a piece of small intestinal submucosal (SIS) tissue adjacent to the heart, having a size and configuration that will render the SIS tissue suitable for implantation as a replacement mitral valve.

This invention comprises a method of using tubular material to replace heart valves during cardiac surgery. In one preferred embodiment, a segment of small intestinal submucosal (SIS) tissue is used. If desired, the SIS tissue can be harvested from the body of the same patient who is receiving the replacement valve. This eliminates the risk of immune rejection and the need to use fixation treatment to reduce the antigenicity of tissue from animals or cadavers.

As used herein, "tubular starting material" refers to material that is harvested from a human or animal body in tubular form (such as intestinal tissue), and to synthetic material that is synthesized, molded, woven, or otherwise created in tubular form. Tubular starting material is distinct from flat starting material that has been secured by means such as suturing into a tubular intermediate form.

This approach to using tubular material is substantially different from all artificial valves (mechanical or tissue) that are available for human use today. It is based upon the recognition of a fundamental principle of native heart valve structure and function, which either has gone unrecognized or which has been sacrificed and lost when compromises were required to adapt available materials to surgical requirements. The basic principle, as described in the Background section, is that "Form Follows Function." If an artificial valve can be created that truly functions like a native valve, its resultant form will, of necessity, be similar to that of a native valve.

To assess and display the "Form Follows Function" principle mathematically, a flexible tubular segment was created in a three-dimensional CAD-CAM program, which was run on a computer in the Applicant's research laboratory. The tube segment was affixed, at certain designated points, to the interior wall of a cylindrical flow conduit. One end (corresponding to the inlet) of the flow conduit and flexible tube were flattened on one side, and the flexible tube inlet was fixed around the entire inner circumference of the flow conduit. The other end (the "outlet") of the flexible tube was fixed at only two opposed points inside the flow conduit. An external force of 120 mm Hg (corresponding to the pressure generated in the left ventricle during systolic contraction of the ventricle) was applied to the outlet end of the flexible tube, and all unattached areas of the flexible tube were allowed to flex and move according to the mathematical deformations and constraints that occurred as a result of the imposed conditions. The program used an iterative finite-element algorithm to determine where each square in an imaginary grid on the surface of the flexible tube would be located. It was allowed to run to completion, which took approximately 12 hours. At the end of these calculations, the wall of the tube was visually depicted by the computer, and the resultant shape of the tube perfectly resembled the shape of a mitral valve when closed by back-pressure in a left ventricle.

A similar CAD-CAM analysis was performed for an aortic (or pulmonary) valve in which the inlet end of the flexible tube was fixed circumferentially around the inlet of the flow conduit, and the other end of the flexible tube was fixed at 3 equidistant points around the circumference of the conduit. The external pressure applied to the outside of the tube was 80 mm Hg, corresponding to the arterial pressure exerted on normal aortic valve leaflets during diastole. Again, the resultant shape of the tube after 12 hours of mathematical deformation appeared to exactly mimic a natural aortic valve.

Until the CAD-CAM studies had been performed, the relationship of the principle of "Form follows Function" to the form and function of native human heart valves was only a hypothesis. However, the fact that the simple tubes, fixed in a known anatomic manner, were deformed by physiologic pressures into a shape that exactly mimicked the shape of native heart valves confirmed two aspects of the hypothesis in a convincing manner: 1) native heart valves do in fact function like the sides of compressed tubes when they close, and 2) the engineering principle of Form Following Function is applicable to native human heart valves.

To the best of the Applicant's knowledge, the significance of the in utero development of native heart valves as the remnants of simple tissue tubes, and the principle of using tubular structures to replace defective heart valves in an effort to reproduce the function of the native valves, has not previously been recognized or disclosed. The most closely related effort at creating artificial heart valves were described in Mickleborough et al 1989, which was discussed in the Background section. However, they did not use tubular material as the starting material; instead, they used bovine pericardial material, which is effectively flat. That approach required the used of animal tissue that had been treated with chemicals (glutaraldehyde) to reduce its antigenicity.

The approach described in Mickleborough et al 1989 also required the creation of a suture line to convert the flat pericardial tissue into a quasi-tubular structure. This created certain problems and risks, since a longitudinal suture line requires additional handling of the pericardial material by surgeons. This additional handling would need to be done after the patient's chest and heart have been surgically opened, therefore increasing the time during which the patient needs to be kept on cardiopulmonary bypass (CPB). As is well known, any increase in the length of time of artificial circulatory support is adverse, and any reduction of the time required for keeping a patient on CPB is beneficial. In addition, the creation of a longitudinal suture line during a mitral or tricuspid valve replacement might increase the risk of tearing the leaflet material at the suture points, and the risk of thrombosis. For both of these reasons, the use of tubular starting material (such as intestinal tissue) as described herein, rather than flat starting material, is advantageous, provided that the intestinal tissue segment has a diameter compatible with the valve being created. As discussed below, if the diameter of a patient's autologous intestinal segment is not compatible with the diameter of the annulus of a heart valve being replaced (which is likely when aortic or pulmonary valves are being replaced), a pre-treated packaged segment of SIS tissue having the desired diameter from an animal (such as a pig) or a human cadaver can be used to avoid the need for using a longitudinal suture line to convert flat material into tubular material.

Figure 2:
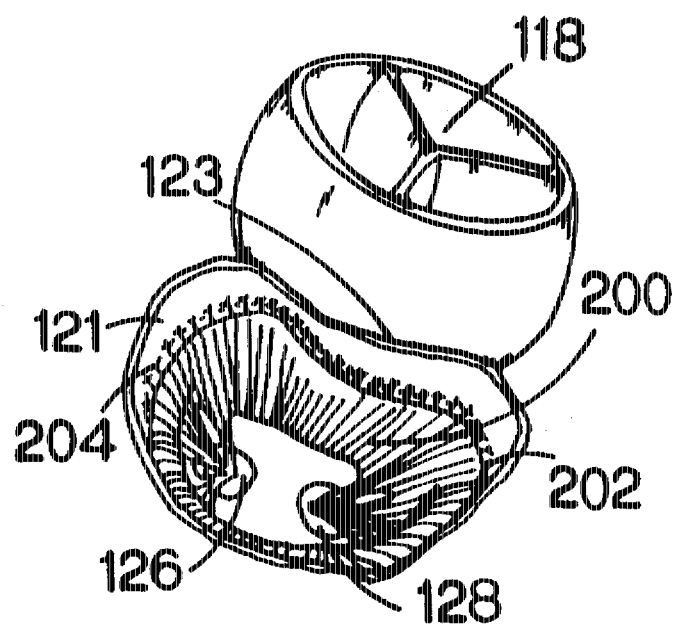
FIG. 2 depicts a top view (from the left atrium) of a tubular tissue valve sutured into the mitral position, showing the orientation of the anterior and posterior leaflets in relation to the anterior and posterior papillary muscles.
Figure 3:
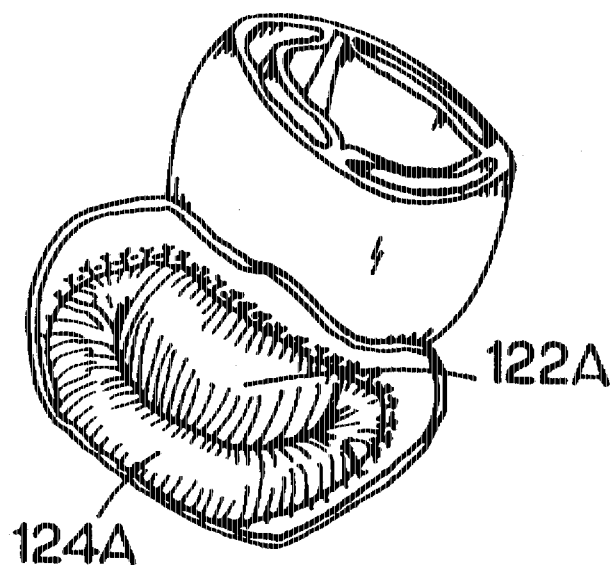
FIG. 3 shows a top view of the tubular mitral valve during systolic contraction of the ventricle. The two leaflets are pressed against each other in a natural "smile" configuration; this closure (approximation) of the leaflets prevents blood from flowing back into the atrium.

In comparing the subject invention to the prior art of Mickleborough et al, it should also be kept in mind that the approach used by Mickleborough et al caused the anterior and posterior leaflets of their replacement valve to be rotated roughly 90° compared to the native leaflets in a native mitral valve. By contrast, the subject invention allows the creation of mitral leaflets having a natural orientation. This factor was discussed in the Background section and is depicted in FIGS. 2 and 3.

Use of Intestinal Tissue

This invention teaches a method for replacing heart valves using tissue from the body of the same patient who receives the replacement valve. In one preferred embodiment, a segment of tissue several inches long is removed from the jejunal or ileal region of the small intestine. Referring to the drawings, item 200 in FIG. 1 refers to a cylindrical (tubular) segment of tissue that has been surgically removed from the jejunal portion of the small intestine (i.e., the extended segment between the duodenal region near the stomach, and the ilial region). The jejunal region of the small intestine is approximately 6 meters (20 feet) long in an adult, and the removal of a short segment (such as about 15 cm, or 6 inches, which would provide more than enough SIS tissue to create a replacement valve) will not significantly affect the digestive capabilities of the patient.

This segment of intestinal tissue can be removed from the patient's abdomen during the same surgical operation used to replace the heart valve. Therefore, only one operation under general anesthesia is required, and the intestinal tissue is fresh and unaltered by storage and/or fixation when it is harvested for immediate use. To complete the abdominal portion of the operation, the small intestine segments on each side of the removed portion are anastomosed (sutured together) using standard techniques, and the abdomen is closed. This entire abdominal portion of the operation can usually be performed in the time it takes to open the chest and cannulate the heart and great vessels in preparation for valve replacement.

After it is resected, the intestinal segment is wiped with a sterile cloth on the outside, to remove two outer layers of tissue known as the serosa and the muscularis (smooth muscle). The segment is then turned inside out and wiped again to remove the mucosal layer that lines the inside of the intestinal segment. Tests using animals have indicated that all three of these layers of the intestinal wall can be wiped off easily and without damaging the basement membrane or submucosa, by a simple wiping procedure. In tests on dogs, the wiping and cleaning procedure has taken only a few minutes.

After the serosa, muscularis, and mucosal layers have been removed, two layers remain in the tissue segment. If the tissue segment is returned to its original orientation, these two layers are the basement membrane (on the outside of the tube) and the submucosa (inside the tube). These two layers form a tough, durable, highly flexible tissue segment, referred to herein as "Small Intestine Submucosa" (SIS) tissue. Anyone other than a surgeon who has worked with intestinal tissue probably would be surprised by the strength and toughness of an SIS tissue segment. It appears to be an ideal material for creating artificial tissue valves for hearts.

Due to the microscopic structure of the collagen fibers in intestinal tissue, it is possible that the life of a replacement valve might be extended if the intestinal tissue segment is turned inside out before being inserted into a heart as a replacement valve. That option can be evaluated, if desired, using routine experimentation.

In addition, other types of preparative steps can also be used to treat the tissue if desired, such as glutaraldehyde or other crosslinking treatment. Such treatment is not necessary to reduce the antigenicity of the tissue, if the tissue comes from the same body that will be receiving the valve; however, as mentioned in the Background section, some reports suggest that treatment with a crosslinking agent such as glutaraldehyde can provide a useful degree of crosslinking between adjacent collagen fibers, which can reduce the tendency of certain types of tissue to shrink or thicken over prolonged periods of time. Apparently, not all types of tissue benefitted from such treatment; accordingly, the effects of glutaraldehyde or other crosslinking treatment on SIS tissue (or other types of tubular tissue) can be evaluated, using routine experimentation on animals, to assess the effects of such treatment on SIS or any other form of tubular tissue when such tissue is used to create a replacement valve. By controlling the concentration of the crosslinking agent and the time and temperature of the crosslinking reaction step, the extent of crosslinking can be controlled. Love and Love 1991 described a crosslinking step that lasted 5 minutes, using 0.6% glutaraldehyde buffered to pH 7.4. Those parameters apparently gave satisfactory results in the experiments involving pericardial tissue. Similar conditions can be tested with SIS tissue, and varied within reasonable limits.

Methods of Implantation

Figures 7, 8:
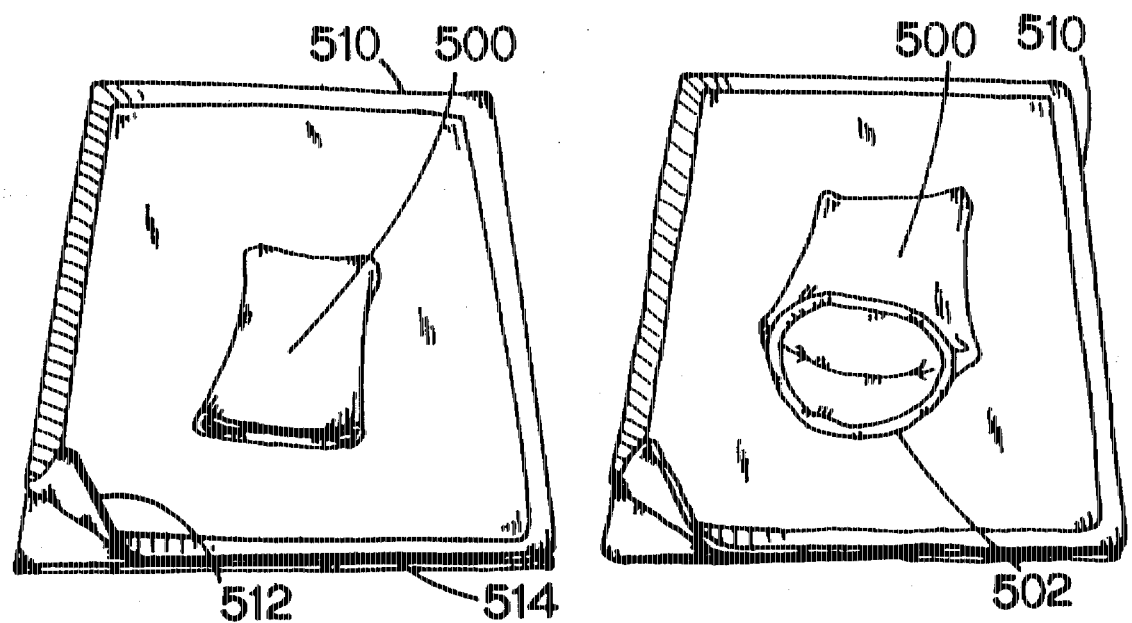
FIG. 7 depicts a tubular segment of intestinal or synthetic material, enclosed within a sealed pouch that maintains sterility of the tubular segment.
FIG. 8 depicts a tubular tissue segment of intestinal or synthetic material which has been attached to an annuloplasty ring, enclosed within a sealed sterile pouch.

The SIS tissue segment can be implanted in a mitral valve position using any of several methods. In one method, it can be initially implanted as an unsculpted tube, then trimmed as necessary to preclude redundancy of the leaflets. This method can be performed as follows. The patient or animal is placed on total cardiopulmonary bypass so that the heart can be opened safely. The heart is either arrested or fibrillated and the mitral valve is exposed through an incision in the left atrium. The leaflets and chordae tendineae of the native mitral valve are surgically removed, leaving behind a mitral valve annulus 121. This annulus 121 has a roughly circular shape; however, as shown in FIG. 2, there is a somewhat "flattened" area 123 in the annulus, on the side closest to the aortic valve In an intact native mitral valve, the base of the anterior leaflet is attached to this "flattened" region of the mitral valve annulus. The inlet (proximal) 202 end of the tubular segment 200 is sutured into the mitral valve annulus 121, using a suture line 204 which travels around the entire circumference of the annulus 121 and the tubular segment 200. If desired, an annuloplasty ring (such as illustrated in FIG. 8) can be used to create a bridge between the valve annulus 121 and the SIS tissue inlet 202.

After the annulus has been properly secured, the length of the SIS segment can be trimmed to eliminate most of the excess length while retaining adequate tissue for the surgeon to work with. Sutures are then used to temporarily secure the outlet (distal) end of the tube to the papillary muscles at a distance from the mitral annulus compatible with the desired degree of "closure" of the tubular valve. This can be done by placing a tacking suture through the appropriate side of the tube distally and then passing it through the tip of the anterior papillary muscle 126. The same procedure is performed on the opposite side of the tube, temporarily attaching it to the posterior papillary muscle 128.

Saline is then injected into the left ventricular chamber 112, which will remain capable of sustaining fluid pressure inside a closed chamber if access to the mitral valve is obtained via an incision through the left atrial wall. The saline flush generates fluid pressure in ventricle 112, which causes the sides of the tube to be forced into approximation. In other words, the saline flush closes the newly-created valve.

Once the proper site of attachment of the distal end of the tube 200 to the two papillary muscles 126 and 128 has been determined, the tube 200 can permanently attached to the tips of the papillary muscles 126 and 128. This can be done in any of several ways. If the distal end of the SIS tissue has been carved, trimmed, or sculpted to create elongated wedges or strands of tissue which will serve as substitute chordae tendineae for attachment purposes, the distal ends of the sculpted tissue segments can be sutured to the papillary muscles. If desired, the tips of the tissue segments can be inserted into small incisions in the tips of the papillary muscles; these can then be reinforced using reinforcing devices on the outsides of papillary muscles, to reduce the risk of tearing the tissue segments or the tips of the papillary muscles.

Alternately, preliminary tests on animals indicate that in animals which have normal papillary muscles of sufficient length, the distal end of the SIS tube does not need to be trimmed to create elongated wedges or strands of tissue for attachment purposes. If the blunt end of an SIS tube is sutured to the anterior and posterior papillary muscles, this will effectively create anterior and posterior leaflets that will emulate native leaflets after the heart starts beating again. Even if no tissue between the two leaflets is removed, it appears that a sufficiently large flow channel can be provided between the papillary muscles to handle the necessary flow.

Accordingly, it does not appear to be essential to remove such tissue by a sculpting or trimming procedure. Nevertheless, a sculpting or trimming step which physically divides the replacement leaflets into an anterior leaflet that has been partially divided from the posterior leaflet is presumed to be preferable, because it can help the valve leaflets more closely emulate the physical shape of the leaflets in a native mitral valve. If such a sculpting or trimming step is desired, it can be carried out at any suitable time during the operation, such as immediately after a temporary suturing step followed by a saline flush have confirmed that a certain attachment configuration will function in the desired manner.

After the SIS tissue has been permanently sutured to the papillary muscles, and after any trimming or sculpting step has been completed, the left atrium is closed and the heart is restarted. During each heartbeat, as blood crosses the valve in a forward direction, because of diastolic expansion of the ventricular chamber and contraction of the left atrium, the leaflets will be forced open.

It should be noted that this tubular valve, when open during the systolic phase of each heartbeat, has no obstructions in its flow path. By contrast, in every type of artificial mechanical valve being used today, various devices must be positioned in the flow path of the blood. These hinder blood flow, leading to pressure gradients across the valve, especially at high flow rates and with small sized valves, and they also generate turbulence that can damage blood cells. Moreover, since previous artificial tissue valves require stents and do not mimic the function of native valves, they also cause turbulence in blood flow, an important factor in the production of calcification in the leaflets of the artificial tissue valve.

As soon as ventricular expansion is complete and systolic contraction of the ventricle begins, the pressure generated inside the ventricle will press the two sides of the tube 200 against each other, closing the valve and forcing the blood to exit the ventricle through the aortic valve in the normal and proper manner. FIG. 3 shows a top view (from the left atrium) of the closed valve during contraction of the ventricle. The two sides of the tube effectively create a new anterior leaflet 122A and a new posterior leaflet 124A, which closely emulate the shapes and orientations of the native anterior leaflet 122 and the native posterior leaflet 124. Closure (approximation) of the replacement leaflets 122A and 124A against each other, caused by the pressure of the blood inside the ventricle, prevents backflow of blood (regurgitation) back into the left atrium.

In a native mitral valve, the commissure between the two natural leaflets is curved, in a manner that resembles a smile. This occurs because: 1) the mitral valve annulus 121 is not completely round, and has a "flattened" region 123 on the side closest to the aortic valve, and 2) pressure on the outside of any tube that has one flat side and is attached at two points distally (in line with the two ends of the flat side) will result in apposition of the two sides of that tube in a manner that resembles a smile. In a simple tube, this results in the side of the tube that is flattened occupying the majority of the orifice. In the case of the mitral valve, it results in the anterior leaflet being larger than the posterior leaflet, thereby occupying the majority of the valve orifice in the closed position. As shown in FIG. 3, this same type of "smile" commissure between the two leaflets is created by proper insertion and attachment of the replacement valve.

In some situations, it may be necessary to resect a small portion of the distal anterior wall of the SIS tube to prevent "systolic anterior motion" of the new anterior leaflet during systolic contraction of the ventricle. The phenomenon of systolic anterior motion of the anterior leaflet, which can lead to interference of blood flow through the aortic valve, is part of the etiology of a certain condition called Hypertrophic Obstructive Cardiomyopathy (HOCM), which affects some patients, and it must be avoided in patients who are likely to be subject to such a condition.

Tricuspid Valve Replacement

Tricuspid valve replacement in humans is especially problematic because tissue valves tend to fail earlier and mechanical valves tend to form clots at a much higher rate than either do in the mitral or aortic position. In addition, when tricuspid valves require replacement for infection, re-infection of the new artificial valve is so common that some authors have actually advocated removal of an infected native valve without replacement with a new artificial one! Thus, the need for a satisfactory artificial valve for tricuspid valve replacement is especially acute.

Tricuspid valve replacement can be created in essentially the same manner as mitral valve replacement, described above. Preliminary studies on animals indicate that the natural shape of the tricuspid annulus at the proximal end of a tube valve and three points of fixation distally to the normal papillary muscles in the right ventricle will result in an anatomically correct trileaflet tricuspid valve. However, it should be recognized that in the right ventricle, papillary muscles are more variable and unpredictable in their placement than in the left ventricle; accordingly, tricuspid valves tend to be more difficult to replace than any of the other three valves, and successful replacement depends even more heavily upon the experience and expertise of the surgeon in tricuspid valve repair than in other valves.

Optional Use of an Annuloplasty Ring for Replacement of Atrio-ventricular Heart Valves A preferred mode for surgical insertion of the valves described herein completely avoids the use of an annuloplasty ring. As foreign objects that come into direct contact with blood (and which typically have rough surfaces, to facilitate sewing), annuloplasty rings in the mitral or tricuspid position pose a theoretical problem in regard to the threat of thrombosis. Accordingly, by disclosing replacement valves that can be created without using annuloplasty rings, this invention offers an advance over prior art replacement valves currently in use.

However, clinical practice has shown that any potential increase in the threat of thrombosis due to an annuloplasty ring in a mitral or tricuspid valve repair is moderately low; by way of illustration, surgeons often conclude that the increased risk of spontaneous hemorrhage associated with systemic anticoagulation outweighs the risk of thrombosis resulting from the use of annuloplasty rings. Accordingly, annuloplasty rings are widely used without severe adverse effects, and in many patients suffering from heart disease or congenital abnormalities, they can be advantageous or even necessary.

Therefore, this invention discloses (1) replacement valves made of tubular tissue (or suitable synthetic material) coupled to annuloplasty rings, and (2) a method of surgically implanting such replacement valves. In such cases, the tubular tissue will work in the same manner as described above, while the annuloplasty ring will help create a bridge between the inlet end of the tubular tissue segment, and a valve annulus in a patient (such as a patient whose native mitral valve annulus is weak, dilated, and/or "rounded" out of its normal shape. The implantation of the annuloplasty ring can be carried out using the same techniques that are currently used for mitral and tricuspid valve reparative techniques. After a segment of SIS tissue has been harvested from the body of the patient receiving the heart valve, the inlet rim of the SIS tissue is sutured to an annuloplasty ring. After the annuloplasty ring has been sutured to an atrioventricular valve annulus, the distal end of the SIS tissue is sutured to the papillary muscles as described above.

Alternately, if synthetic material or an SIS tissue segment from an animal or human cadaver is used, the annuloplasty ring can be coupled to the tube and both can be packaged together in a sealed package which maintains their sterility. This article of manufacture is described in more detail below and is shown in FIG. 8, in which a tubular segment 500 has been attached to an annuloplasty ring 502. Accordingly, the subject invention discloses a method of using small intestinal submucosal (SIS) tissue in conjunction with an annuloplasty ring to create a heart valve replacement.

It should be noted that the tubular valves of this invention do not require stents. As used herein, the term "stent" includes any man-made device (other than a suture, annuloplasty ring, or leaflet material) which is surgically implanted in a patient's heart (or aorta or pulmonary artery) as part of a replacement valve, and which is contacted by blood which flows through the heart (or aorta or pulmonary artery). Stents are major components in all mechanical replacement valves, since they must securely hold the ball, flapper, or other movable elements of the valve in proper position; they are also used in nearly every type of artificial tissue valve, to secure the tissue flaps in the proper configuration. The term "stent" does not include reinforcing pledgets placed on the outside of an aorta or pulmonary artery, since such pledgets would not be contacted by blood flowing through the artery.

Stents are known to increase turbulence and thrombosis. Since the valves disclosed herein are stentless, this invention offers an important advance over prior art replacement valves which are currently approved by the FDA.

In summary, the steps for creating an atrioventricular (mitral or tricuspid) replacement valve can be described as follows:

1. A tubular segment is obtained, consisting of thin and flexible tubular tissue or synthetic material, having an inlet end and an outlet end.

2. The damaged or deformed leaflets of the native diseased valve are surgically removed from the heart of the patient, to generate an open valve annulus. The chordae tendineae are also removed, while the papillary muscles in the ventricular chamber are left intact.

3. The inlet end of the tube is sutured to the valve annulus, or to an annuloplasty ring if necessary for a specific patient.

4. The outlet end of the tube is sutured to the papillary muscles, in a manner which will allow the outlet flaps to function as valve leaflets that will open during ventricular diastole, when blood flows from the atrium into the ventricle. The valve leaflets will approximate and close the valve during ventricular systole, to prevent backflow when fluid pressure in the ventricle exceeds fluid pressure in the atrium. The specific sites of attachment of the tubular material to the papillary muscles should allow the resulting leaflets to approximate in a manner that emulates the shape and angular orientation of the leaflets in a properly functioning native valve.

Aortic (and Pulmonic) Valve Replacement

In a preferred method of creating a replacement for a semilunar valve (i.e., an aortic or pulmonary valve), a segment of intestinal tissue several inches long is removed from the patient and treated to remove the serosa, smooth muscle, and mucosal layers in the same manner described above. This leaves a tubular structure made of the basement membrane and submucosal layers, referred to herein as small intestinal submucosal (SIS) tissue. Alternately, as with atrioventricular tubular valves, the tubular material may be obtained from other animals or from human cadavers, or it may be manufactured from a suitable synthetic material. For convenience, the discussion below will assume that an SIS segment is used. The desired length can range from about 2 cm for neonates to about 6 cm for adults.

Figure 4:
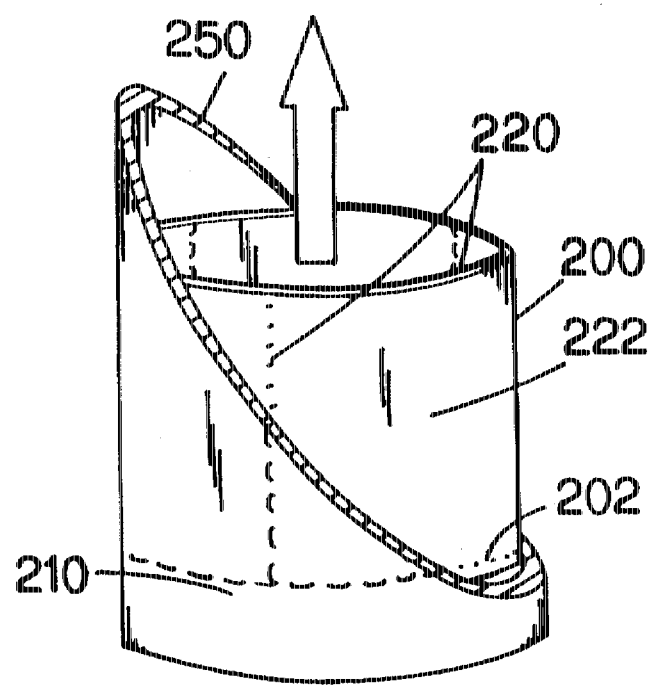
FIG. 4 depicts a tubular segment of small intestine submucosal (SIS) tissue that has been inserted into an aorta or pulmonary artery, to create a semilunar valve with cusps.
Figure 5:
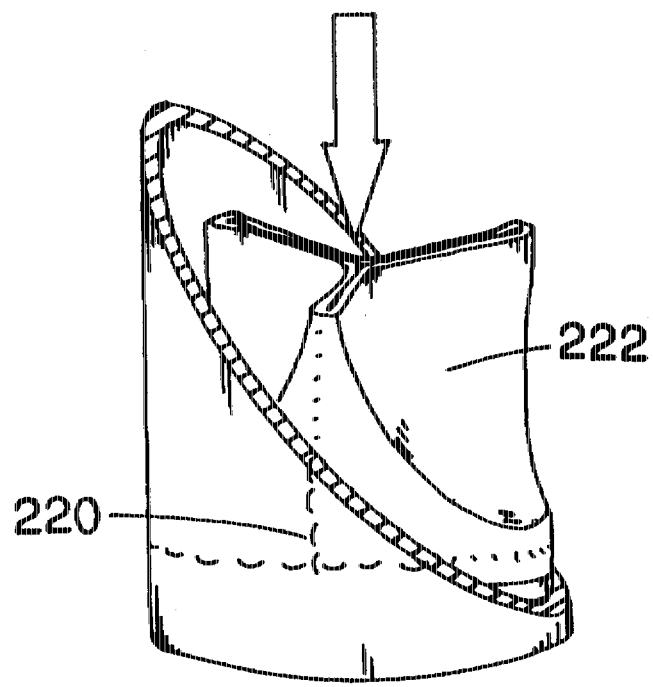
FIG. 5 depicts a semilunar valve as described herein, in a closed position.

To secure a tubular segment 200 inside an aorta (the same approach is used to create a pulmonic valve in a pulmonary artery), an aortic wall is opened by an incision above the level of the commissural posts of the aortic valve, and the cusps of the native aortic valve are removed, leaving behind a valve annulus. The tubular SIS segment 200 is then inserted, and as shown in FIGS. 4 and 5, the inlet end 202 is secured to the interior surface of the aortic wall 250 by means of a circumferential suture line 210; this step can utilize an annuloplasty ring if desired. If desired, the SIS segment can then be secured by means of three longitudinal suture lines 220 spaced at one-third intervals (120° apart from each other) around the internal periphery of the aortic wall 250.

Suturing the tissue segment 200 to the inside of the aortic (or pulmonary artery) wall 250 by means of three longitudinal suture lines 220 will leave three tissue regions 222 which will function as cusps during operation of the valve. After the tissue cylinder 220 is properly secured and the patient's heart is closed by the surgeons and restarted, the three cusp regions 222 will go through a cyclical movement with each heartbeat. During the systolic stage (ventricular contraction) of each heartbeat, depicted in FIG. 4, the cusps 222 be held open by blood entering inlet end 202 and exiting outlet end 204. When the systolic stage ends and the left ventricle begins to expand during diastole, back pressure in the aorta (or pulmonary artery) causes the three cusps 222 to flex in a downward and inward direction; however, the cusps are constrained and their motion is limited by the three longitudinal suture lines 220. The combination of pressure and tension causes the three cusps 222 to flex inwardly, as shown in FIG. 5, thereby closing the valve and preventing backflow into the ventricle.

An alternative to placing the three parallel rows of suture lines inside the aorta (or pulmonary artery) as described above is to fix the outlet end of the tube valve at three equidistant points (120° apart around the circumference of the outlet end) only. This technique will preclude the necessity for the longitudinal suture lines described above but will allow the valve to function in the same manner.

If desired, the three longitudinal suture lines 220 (or the three points of fixation of the outlet end of the tube) can be reinforced by strips (often called pledgets) placed on the exterior of the aortic wall. These reinforcing strips can be made of autologous tissue, materials sold under trademarks such as TEFLON, GORETEX, SILASTIC, or any other suitable material. Since these strips would be positioned outside the aorta or pulmonary artery, they would not come into contact with blood flowing through the artery. Therefore, they can reinforce the arterial wall, distribute any tensile stresses more evenly across a wider area of the arterial wall, and reduce the risk of tearing the arterial wall, without increasing the risk of thrombosis inside the artery. Depending on the positioning of the replacement valve in the aorta, it may also be desirable to place a similar strip around the exterior of an aorta or pulmonary artery to reinforce the circumferential inlet suture.

If a need becomes apparent in a specific patient, similar reinforcing strips can also be positioned inside an aorta or pulmonary artery, and a stent can be used to reinforce the inlet attachment. However, any reinforcing component which is exposed to blood inside the artery would increase the risk of thrombosis and probably would suggest to the surgeon that the patient would need to be placed on anticoagulant drugs to reduce the risk of clot formation.

In some patients, it may be preferable to use an annuloplasty ring for replacement of an aortic or pulmonary valve. Accordingly, the subject invention discloses a method of replacing the aortic and pulmonary valves in which a round annuloplasty ring is used in conjunction with the artificial tubular tissue or mechanical valve. After obtaining a tubular segment of tissue or synthetic material, the tubular segment is sutured at its inlet end to a round annuloplasty ring which is then sutured into the aorta (or pulmonary artery) at the level of the lowest point of the excised native semilunar valve. The distal end of the tubular segment for both aortic valves and pulmonary valves is then handled in the same manner as described above for these valves without annuloplasty rings.

Two additional variations in aortic and pulmonary replacement valves have been recognized and will be evaluated if an apparent need arises. First, initial tests on dogs, coupled with computer analysis using an iterative finite-element algorithm to calculate the stresses on each portion of a cylindrical tissue segment constrained as described herein, have indicated that satisfactory results are obtained if the outlet end of the tissue cylinder is cut in a planar manner, perpendicular to the main axis of the cylinder. This can be regarded as a blunt-end or square-end cut. As an alternative method of sculpting the tissue segment, non-planar cuts (such as a mildly sinusoidal cut) can be used to generate three flaps of tissue that extend slightly beyond the outlet ends of the longitudinal suture lines (or fixation points) or to slightly scallop the outlet end of the tube valve, as is more characteristic of the native semilunar valves. Non-planar outlets have not yet been evaluated, but they can be tested using any of several techniques (computerized CAD-CAM analysis, in vitro testing using a closed mechanical pumping circuit, or in vivo using animals such as dogs or sheep) to determine whether they are preferable to a square-end outlet, either for particular patients or as a general approach.

In summary, the steps for creating a semilunar replacement valve (i.e., an aortic or pulmonary valve) can be described as follows:

1. A tubular segment is obtained, consisting of thin and flexible tissue or synthetic material having an inlet end and an outlet end.

2. The damaged or deformed leaflets of the native valve are surgically removed, to generate an open valve annulus.

3. The inlet end of the tube (or an incorporated annuloplasty ring) is sutured to the valve annulus.

4. The outlet end of the tube is sutured to the aorta or pulmonary artery at three equidistant points around the circumference. This creates three outlet flaps between the three points of attachment, and the outlet flaps will function as valve cusps that will open during ventricular systole, when blood flows from the ventricle into the aorta or pulmonary artery. The valve cusps will approximate and close the valve during ventricular diastole, to prevent backflow when fluid pressure in the aorta or pulmonary artery exceeds fluid pressure in the respective ventricle.

Based on the information available to date, including animal tests as well as computer simulations and the Applicant's extensive experience in cardiac surgery, it appears that it is not necessary to provide any additional safeguards to ensure that the three cusp regions in a replacement aortic or pulmonary valve come together and close during each diastolic cycle, rather than being flattened against the inside of an aortic wall (or pulmonary artery wall). Nevertheless, it is recognized that if the back pressure in the aorta were to flatten any of the three cusp regions against the artery wall, rather than causing all three to close together, closure of the valve would be prevented and regurgitation (i.e., reentry of the blood into the ventricle) would result. Accordingly, if it is desired to increase the level of assurance that flattening of the cusps against the interior wall of the artery will not occur during diastole, either as a general precaution or in patients having certain abnormal conditions, then at least two methods are available to reduce such risks.

Figure 6:
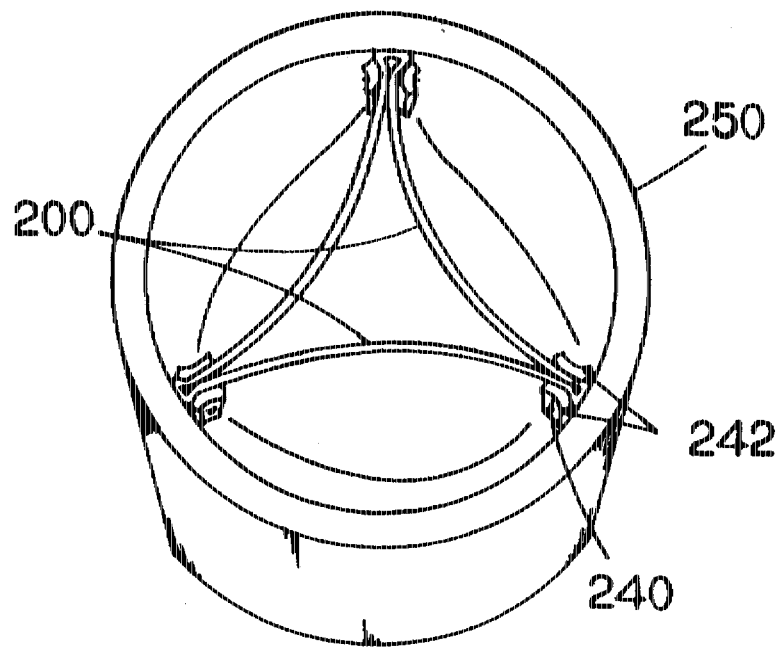
FIG. 6 depicts a configuration that can be used if desired to secure tubular tissue inside an aorta in a configuration in which the cusps of the valve are pinched together adjacent to the arterial wall.

The first method involves creating a partial closure of adjacent cusps at their outer periphery. This can be done by gently pinching the walls of the inserted SIS cylinder 200 together at the outlet end of each of the three longitudinal suture lines 220 (or outlet attachment points), as shown in FIG. 6. The pinched SIS junctures can then be held in place by one or more suture stitches 240. If desired, the suture stitches 240 can be reinforced to prevent tearing of the SIS segment 200 by placing small reinforcing pieces 242, made of a flexible, soft, blood-compatible material such as Gore-Tex or Silastic, on the outside surfaces of the SIS wall 200, as shown in FIG. 6.

An alternate potential method for ensuring that the three cusps will not become flattened against the inside of the aorta (or pulmonary artery) involves a stent device that could be secured within the aortic wall 250, outside the SIS segment 200. This type of stent, if used, would containing projections which extend in an inward radial direction, toward the central axis of the aorta. These projections, which would be positioned at midpoints between the three attachment points at the outlet end, would prevent any flattening of the cusp regions 222 against the interior of aortic wall 250. This would ensure that back pressure in the aorta would force each cusp in an inward direction, to ensure closure, rather than pressing the cusps in an outward direction which would cause them to flatten against the interior of the arterial wall and allow regurgitation.

The use of such a stent probably would require placing the patient on anticoagulant drugs to reduce the risk of thrombosis. Nevertheless, the blood would not be forced to flow through any mechanical elements as are currently used in conventional caged-ball, bi-leaflet, or tilting disk valves; instead, the blood would flow through a cusp arrangement which uses soft, flexible cusps. Therefore, this approach, even though it would require a stent outside the cusps to ensure closure, would probably provide a valve that is less thrombogenic and less hemolytic than any currently available mechanical valves.

Reduction of Turbulence and Calcification by Tubular Valves

In addition to the various problems (particularly lack of durability) that are characteristic of conventional tissue valves in use today, it also appears that their designs may aggravate the problem of calcification, a major pathologic form of deterioration which leads to the failure of many presently available artificial tissue valves. Previous analyses regarding the etiology of calcification of artificial tissue valves have centered around (1) the tissues used to construct the valves, which presently are either porcine valve cusps or bovine pericardial tissue; (2) chemical fixation processes which are necessary to render heterograft tissues non-antigenic, or (3) non-chemical fixation processes, usually involving freezing, which are necessary to treat homograft tissues to reduce their antigenicity.

However, a highly important piece of evidence indicates that another factor is etiologically significant in tissue valve calcification, namely, the turbulence of blood flow that occurs within and around all artificial tissue valves constructed using prior art designs. Evidence that turbulence can cause or severely increase the risk of valve calcification in the absence of foreign material, fixation techniques, and antigenicity, is provided by the fact that over half of the patients who must undergo surgery for calcific aortic stenosis were born with a bi-leaflet aortic valve, a condition which is notorious for causing turbulent flow. In these patients, neither antigenicity nor fixation processes can be incriminated as causes of valve calcification, since the patient's own valve is the one that has calcified. Therefore, the high rates of calcification encountered in abnormal bi-leaflet aortic valves offers strong evidence that turbulent blood flow, per se, can cause or severely increase the risk of calcification of valves.

Preliminary studies suggest that by reproducing the manner in which native valves function, less turbulence will be generated as blood passes through the valves disclosed herein, compared to conventional replacement valves. Therefore, it appears likely that this reduction in turbulence will, in turn, reduce the likelihood that the tubular tissue valves described herein will calcify.

Use of Intestinal Tissue in Heart Valves

To the best of the Applicant's knowledge, it has never previously been disclosed or suggested that autologous human intestinal tissue, specifically the submucosa of the small intestine (SIS), can or should be used to create all or part of a replacement artificial heart valve in a patient with a defective or diseased heart valve. Since autologous intestinal tissue, when harvested and treated as described above, appears to be very well suited to this use, and since it offers a number of important advantages over materials used in conventional heart valve replacements (including the complete absence of antigenicity, and the absence of the requirement of chemical fixation of the tissue prior to implantation), an important aspect of this invention is the disclosure, in broad terms, that intestinal tissue harvested from the body of the same patient who is receiving a new heart valve can be used in the replacement valve.

Accordingly, this invention discloses a method of surgically replacing a heart valve in a human patient in need thereof, comprising the steps of (a) extracting a segment of intestinal tissue from the patient's abdomen, and (b) using the intestinal tissue to form at least one component of a replacement valve for the patient's heart. It also discloses certain articles of manufacture comprising previously prepared intestinal segments, from animals or human cadavers, which have been treated to render them suitable for use in creating replacement valves, and which are contained in sealed packages that maintain their sterility. These articles of manufacture are discussed in more detail below.

Other Tissue Sources

Although autologous SIS intestinal tissue described above appears to be an ideal tissue for creation of artificial tissue valves, the critical factor in the construction of such artificial tissue valves remains the tubular shape of the tissue or material to be implanted rather than the specific source of origin of that tissue or material.

Various other types of tissue from the body of the patient receiving the heart valve replacement can be used if desired, rather than intestinal tissue. For example, in most patients, the pericardial sac which encloses the heart has enough tissue so that a segment can be removed and used as a heart valve. This would allow a surgeon to conduct the entire operation without having to make an additional incision in the patient's abdomen. In fact, recent studies by others have indicated the feasibility of using freshly harvested autologous pericardial tissue to create artificial cusps that can then be sutured inside the aorta to serve as an artificial aortic valve. That technique, however, differs in several ways from the current invention, and those investigators apparently have not recognized the importance of the principal that Form Follows Function. Their technique is designed to create artificial cusps that look like the native aortic valve cusps from fresh autologous pericardium in hopes that they will function like the native cusps. In other words, their apparent goal and principle is to force function to follow form. By contrast, the subject invention states that pericardial tissue (which is essentially flat) can be used to replace an aortic valve if desired, but the pericardium should first be fashioned into a tube, and that tube should be fixed inside the aorta in the manner described above. By fixing the inlet end of the tube circumferentially and the outlet end of the tube at 3 points (or along three longitudinal lines from the inlet), the external diastolic pressure in the aorta will cause the non-fixed sides of the tube to collapse against one another and the pericardial tube will be forced into the shape of a normal aortic valve. In other words, "Form Follows Function". The principle that Form Follows Function will be operative in all artificial tubular valves used to replace any of the four native valves regardless of the specific type of tissue used to create the tubes.

In view of encouraging results obtained to date with intestinal tissue, and in view of the abundant supply of small intestinal tissue in all patients, other types of autologous tissue have not been evaluated to determine whether they are sufficiently durable and flexible for use as a heart valve. However, if the need arises, other types of autologous tissue can be evaluated using routine experimentation. For example, a potential source of tissue is the "fascia lata," a membranous layer which lies on the surface of certain skeletal muscles.

Another potential source of autologous tissue is suggested by a known phenomenon involving mechanical objects that are implanted in the body, such as heart pacemakers. When such objects remain in the body for several months, they become encapsulated by a layer of smooth, rather homogeneous tissue. This phenomenon is described in articles such as Jansen et al 1989. The cellular growth process can also be controlled by manipulating the surface characteristics of the implanted device; see Chehroudi et al 1990. Based upon those observations and research, it is possible that mandrill implantation in the body of a patient who will need a heart valve replacement might become a potentially feasible technique for generating the cylindrical tissue.

As another potential approach, it may be possible to generate unlimited quantities of cohesive tubular tissue segments with varying diameters, for use in patients of different size, using in vitro tissue culture techniques. For example, extensive work has been done to develop skin replacements for burn victims and tubular vascular grafts, by seeding viable connective tissue cells into lattices made of collagen fibers. Collagen is the primary protein that holds together mammalian connective tissue, and the lattice provides the cells with an environment that closely emulates the environment of natural tissue. The cells will grow to confluence, thereby forming cohesive tissue, and some types of cells will secrete enzymes that gradually digest the artificial collagen matrix and replace it with newly generated collagen fibers secreted by the cells, using the natural process of collagen turnover and replacement. This type of cohesive tissue culture is described in articles such as Yannas et al 1989 and Tompkins and Burke 1992.

Either of these approaches (mandrill implantation or ex vivo tissue culturing) would require careful evaluation to determine whether the resulting tissue would be suitable for long-term use in heart valves. With the promising results obtained to date with intestinal tissue, which is in abundant supply, there does not seem to be an apparent need to undertake such tests at the present time.

In an alternate embodiment of the subject invention, "homograft" tissue can be harvested from the bodies of human cadavers for later use in artificial tubular heart valves. For example, a very long segment of intestinal tissue comprising all or a major portion of the jejunal region of the small intestine can be resected from the body of someone who has recently died, such as an accident victim. This harvesting operation would be comparable to harvesting a heart, kidney, or other internal organ from a deceased organ donor. The intestinal tissue is then cut into segments of roughly 10 to 20 cm (four to eight inches) each, which would then be prepared (by removing the serosa, smooth muscle, and submucosal layers), treated to reduce its antigenicity, and stored (at either refrigerated or frozen temperature) in a sterile preservation solution until use. When needed as a heart valve replacement, the tissue would be warmed and treated as necessary, and cut into the precise size and configuration needed.

One advantage of this approach is that it would spare the cardiac patient from any additional pain or surgical stress that might result from having a surgical incision made in the abdomen to harvest autologous SIS tissue as described above. However, the additional stress or pain of obtaining a segment of intestinal tissue through a small abdominal incision is quite small compared to open-heart surgery, where the chest and rib cage must be opened. Indeed, several of the newest approaches to coronary artery bypass surgery (the most frequently performed cardiac operation) require much larger abdominal incisions to harvest abdominal arteries that are now used as bypass conduits.

Another alternate embodiment is to use "heterograft" tissue from other animal species. This embodiment probably would require chemical fixation of the heterograft tissue (which presumably would comprise intestinal segments) by techniques such as glutaraldehyde crosslinking, as currently used to fix porcine or bovine pericardial tissue for conventional heart valve replacements. Although one might expect intestine-derived tubular tissue fixed in glutaraldehyde to have problems similar to the presently available tissue valves, the calcification and durability problems of current tissue valves should be substantially reduced because of the tubular structure of the resultant valves, which would reproduce the function of the native valves, thereby leading to less turbulence and hence, less calcification, and greater long-term durability. It should also be noted that researchers are creating, using breeding as well as genetic engineering techniques, various strains of animals (mainly pigs) that have reduced tissue antigenicity (see, e.g., Rosengard et al 1992 and Emery et al 1992). Such animals may be able to provide tissue which needs minimal fixation, or possibly no fixation treatment at all.

Tubular "Mechanical" (Non-Tissue) Valves

In addition to providing a method of using tubular human or animal tissue to create replacement valves, this invention also suggests the use of tubular synthetic material as a starting material for such valves. Various types of highly durable and flexible synthetic materials have been developed and are continuing to be developed, and some of these materials are promising candidates which can be evaluated for possible use as described herein. One such material is sold under the trademark "GoreTex." It is, in essence, a polymerized layer of PTFE which is rendered flexible by coating it onto a flexible woven or knitted substrate material, such as nylon fabric. By coating PTFE onto a tubular substrate, it is possible to create tubular forms of such coated materials. Although such materials are highly durable inside the body, they can occasionally causes problems of blood clotting, apparently due in part to their rough surface textures, and possibly due also to plasticizers and other chemicals used to control the polymerization, thickness, and flexibility of the PTFE coating material.

Perfluorinated elastomers, a different class of synthetic materials that have recently been developed, also offer promise as potential artificial tubular valves as described herein. These elastomers are described in patents such as U.S. Pat. No. 4,900,793 (Lagow and Dumitru, 1990). Essentially, they contain only carbon and fluorine atoms, which are bonded together in highly stable polymeric configurations. Perfluorinated elastomers contain very little oxygen, hydrogen, nitrogen, sulfur, or other substances that might chemically react with physiological fluids to degrade the elastomer or cause leaching of constituent ions into the blood. These elastomers can provide very smooth surfaces, and since they are elastomeric in their own right, it is unnecessary to coat them onto the rough surface of a second material such as woven or knitted nylon in order to provide flexibility. They can be molded or otherwise synthesized directly into tubular form.

An additional advantage that can be obtained by using synthetic materials in the manner disclosed herein is that an essentially tubular configuration can be provided which has a gradually varying diameter. For example, a relatively long tubular device can be created from synthetic material, having a diameter at the inlet end of up to about 5 cm and a diameter at the outlet end of about 2 cm. A surgeon can simply cut the piece of tubing at any appropriate location along its length, to provide an inlet diameter corresponding to the diameter of a patient's valve annulus, which can be measured after the heart has been opened and the damaged or defective leaflets have been removed. In this manner, a single tubing size can be adapted to accommodate various different patients; this will reduce the costs that would be required to manufacture or stock tubes having multiple different sizes.

In the case of artificial "mechanical" (non-tissue) tubular valves, the more physiologic flow patterns should result in less thrombogenicity and less turbulence, which are major problems with presently available mechanical valves. The design disclosed herein is, to the best of the Applicant's knowledge, the only mechanical (non-tissue) valve design ever proposed that has absolutely no obstructing part within the flow orifice of the valve in the open position. Conventional mechanical valves require hinge mechanisms, moving discs, large struts, caged balls, or bulky sewing rings, all of which have been incriminated as etiologic factors in the inherent thrombogenicity and/or sub-optimal hemodynamics of previously constructed mechanical heart valves, especially those of smaller sizes. Even the McGoon and Roe-Moore valve designs (described as "extinct" in Bodnar and Frater 1991, pp. 319–321) required obstructions in the flow path; those valves returned to a closed position when at rest, and the leaflets which blocked the flow path had to be forced opened in order for blood to flow through those valves. By contrast, the tubular valves disclosed herein are effectively open when at rest, and the atrioventricular leaflets or semi-lunar cusps close only when they are forced into a closed position by blood pressure. Compared to all previously available or proposed mechanical valves, the mechanical valves disclosed herein will have better hemodynamic characteristics and are likely to be less thrombogenic.

Finally, although the durability of conventional mechanical valves is considered to be their most attractive feature, valve failures do occur. These structural failures are invariably due to high mechanical stresses and/or trauma that are focused on certain points in a given valve design. Such repetitive, focused stresses can eventually result in the failure of the materials used to construct such valves. By contrast, the computerized analytical studies on tubular valves, described above, indicated that the distribution of stress in a tubular replacement valve as described herein is virtually identical to the distribution of stress in native heart valves; such natural stress distributions can be assumed to be optimal. Furthermore, the areas of maximal stress encountered by tubular replacement valves were relatively low in magnitude, since they were distributed over larger surface areas, when compared to conventional mechanical valve designs. Therefore, the fact that tubular replacement valves are stressed in an apparently optimal fashion, as dictated by nature, indicates that they will have less risks of stress-related mechanical failure than conventional mechanical valves.

Articles of Manufacture

In addition to disclosing a method of surgery, this invention discloses an article of manufacture depicted in FIG. 7. This item comprises a tubular segment 500, made of tissue from the small intestine, or synthetic material having suitable overall dimensions and walls sufficiently thin and flexible to allow them to function as leaflets in a heart replacement valve. Since autologous tissue would not require storage for later use, this portion of the disclosure relates to the use of non-autologous (homograft or heterograft) tissue. This tubular segment 500 is enclosed within a sealed container 510 that maintains sterility of the segment 500. Such a sterile container 510 can comprise a plastic pouch, as shown in FIG. 7, having a transparent front layer 512 to allow visual inspection (this layer is shown folded up at one corner, for depiction purposes only). The front layer 512 is sealed around its periphery to a back layer 514.

In an alternate article of manufacture, depicted in FIG. 8, the tubular segment 500 is attached to an annuloplasty ring 502 before both are sealed inside package 510. The tube-to-ring attachment can be done by suturing in the case of tubular tissue segments, or by any suitable synthetic method (such as molding) if a synthetic tube is attached to a synthetic annuloplasty ring.

If intestinal tissue is used, it should be packaged in hydrated form, in a suitable liquid (such as phosphate-buffered saline with one or more preservative agents, such as glutaraldehyde, if desired) contained within the pouch. Such pouches can be shipped and stored in stiff-walled boxes for protection; alternately, instead of using a flexible pouch as the container, a plastic box with a transparent closure layer sealed around its rim can be used as the container itself.

If a segment of intestinal tissue is contained in such a sterile container, it preferably should be treated before being sealed within the pouch, to remove the exterior serosa and muscularis layers and the interior mucosal layer, leaving only the desirable submucosal and basement layers.

In another preferred embodiment involving synthetic materials, a synthetic tube as described herein can have a diameter that varies gradually over its length. Such a tube can be transsected at a location having the desired diameter. This would allow a tube with a single size to accommodate patients who have valve annulus diameters with varying sizes.

In another preferred embodiment involving synthetic materials, different sizes of synthetic tubes can be packaged separately. This raises an important issue. In most cases, it will probably be possible to directly insert an SIS intestinal segment harvested from a patient directly into the mitral or tricuspid valve location in that patient, since the diameters of an SIS segment and a mitral or tricuspid valve annulus in most humans is believed to be comparable or at least compatible. However, this does not appear to be the case with aortic or pulmonary valve replacements; in most patients, the diameter of an SIS segment is likely to be too large for direct insertion in tubular form into the aorta or pulmonary artery of that patient. To cope with this problem, an SIS segment can be cut longitudinally, to convert it into a flat segment that can be trimmed to any desired size before creation of the replacement valve. As described above, three longitudinal suture lines can be used to create a replacement aortic or pulmonary valve, as part of the surgical procedure. Therefore, one of these suture lines can be used to re-size the SIS segment into a different diameter while retaining its tubular form.

Alternately, to replace any of the four heart valves, a prepackaged intestinal tissue segment can be used which has the desired diameter, harvested from a human cadaver or animal. This would avoid the need for a longitudinal cut, and it would preserve the tubular form of the intestinal segment throughout the entire procedure. Tissue from cadavers or animals would need to be treated by fixation (using glutaraldehyde crosslinking or another suitable method) to reduce its antigenicity before implantation.

Accordingly, one of the preferred embodiments of this invention comprises an array of sealed sterile packages containing intestinal tissue segments from cadavers or animals for use in creating replacement valves. Each separate container would hold an intestinal segment having a known diameter or circumference (presumably measured in millimeters), which would be indicated on the label of the container. Before being packaged, the tissue segments would be cleaned to remove the undesired tissue layers and fixed to reduce antigenicity. After a surgeon opens a patient's chest and excises the cusps or leaflets from a diseased or damaged valve, he or she can directly measure the valve annulus. This measurement will indicate the exact diameter or circumference of the intestinal segment that should be used. A sealed package containing an intestinal tissue segment having the desired diameter or circumference can be selected and opened, and the segment will be immediately available. If desired, the tissue segment in the sterile package can already be attached to an annuloplasty ring, which would also be contained in the package.

Accordingly, this invention discloses an article of manufacture comprising a sealed sterile package containing a tubular intestinal tissue segment which has been treated to render it suitable for implantation as a heart valve. The diameter or circumference of the intestinal segment preferably should be indicated on the label of the package, and if desired, the intestinal tissue can be affixed at one end to an annuloplasty ring. To increase the utility of these prepackaged intestinal segments, they can be sold and stored in groups of packages containing tissue segments having various sizes, so that a package containing an intestinal segment having an exact desired diameter or circumference will be available to a surgeon during a cardiac operation even if he cannot specify the exact size before the operation begins.

Thus, there has been shown and described a new and useful article of manufacture and method for create replacement heart valves from tubular tissue or synthetic material. Although this invention has been exemplified for purposes of illustration and description by reference to certain specific embodiments, it will be apparent to those skilled in the art that various modifications and alterations of the illustrated examples are possible. Any such changes which derive directly from the teachings herein, and which do not depart from the spirit and scope of the invention, are deemed to be covered by this invention.

REFERENCES

Bailey, C. P., et al, "Use of autologous tissues in mitral valve reconstruction," *Geriatrics* 25:119–129 (1970)

Bodnar, E. and Frater, R., *Replacement Cardiac Valves* (Pergamon Press, New York, 1991)

Chehroudi, B., et al, "Titanium-coated micromachined grooves of different dimensions affect epithelial and connective-tissue cells differently in vivo," *J. Biomed. Mater. Res.* 24:1203–19 (1990)

David, T. E., "Mitral valve replacement with preservation of chordae tendineae: Rationale and technical considerations," *Ann. Thorac Surg.* 41:680 (1986)

Emery, D. W., et al, "Expression of allogeneic class II cDNA in swine bone marrow cells transduced with a recombinant retrovirus," *Transplant Proc.* 24:468–9 (1992)

Hansen, D. E., et al, "Relative contributions of the anterior and posterior mitral chordae tendineae to canine global left ventricular systolic function," *J. Thorac. Cardiovasc. Surg.* 93: 45 (1987)

Jansen, J. A., et al, "Epithelial reaction to percutaneous implant materials: in vitro and in vivo experiments," *J. Invest. Surg.* 2:29–49 (1989)

Love, C. S. and Love, J. W., "The autogenous tissue heart valve: Current Status," *J. Cardiac Surgery* 6:499–507 (1991)

Mickleborough, L. L., et al, "A simplified concept for a bileaflet atrioventricular valve that maintains annular-papillary muscle continuity," *J. Cardiac Surgery* 4:58–68 (1989)

Miki, S., "Mitral valve replacement with preservation of chordae tendineae and papillary muscles," *Ann. Thorac. Surg.* 25: 28 (1988)

Netter, F. H., *The CIBA Collection of Medical Illustrations, Volume 5: The Heart* (CIBA Pharm. Co., 1969)

Rittenhouse, E. A., "Replacement of ruptured chordae tendineae on the mitral valve with autologous pericardial chordae," *J. Thorac. Cardiovasc. Surg.* 75:870 (1978)

Rosengard, B. R., et al, "Selective breeding of miniature swine leads to an increased rate of acceptance of MHC-identical, but not of class I-disparate, renal allografts," *J. Immunol.* 149: 1099–103 (1992)

Tompkins, R. G. and Burke, J. F., "Burn wound closure using permanent skin replacement materials," *World J. Surg.* 16:47–52 (1992)

Yannas, I. V., et al, "Synthesis and characterization of a model extracellular matrix that induces partial regeneration of adult mammalian skin," *Proc. Natl. Acad. Sci. USA* 86:933–937 (1989)

I claim:

1. A method of surgically creating a replacement heart valve in a patient in need thereof, comprising the following steps:

a. extracting a tubular segment of intestinal tissue from a mammalian abdomen;

b. trimming the tubular segment of intestinal tissue to a size which provides a surgically-implantable segment of intestinal tissue; and, c. surgically securing the surgically-implantable segment of intestinal tissue in the patient, in a position originally occupied by a native heart valve which has been removed, in a manner which causes the intestinal tissue to form a replacement heart valve.

2. The method of claim 1 wherein the surgically-implantable segment of intestinal tissue is used to replace an atrioventricular heart valve having at least two leaflets, wherein a first end of the segment of intestinal tissue is secured to an atrioventricular valve annulus, and wherein a second opposing end of the segment of intestinal tissue is trimmed to provide leaflets which are secured to papillary muscles in a manner which generates a valve outlet end.

3. The method of claim 2 wherein the intestinal tissue is used to replace a mitral valve in a ventricular chamber having an anterior papillary muscle and a posterior papillary muscle, and wherein the intestinal tissue is secured to the anterior papillary muscle and the posterior papillary muscle in a manner that generates an anterior leaflet and a posterior leaflet which, during valve closure, form a line of commissure which closely approximates a natural line of commissure formed by native atrioventricular leaflets during valve closure.

4. The method of claim 2 wherein the first end of the segment of intestinal tissue is secured to the atrioventricular valve annulus using an annuloplasty ring.

5. The method of claim 1 wherein the intestinal tissue is extracted from the patient who receives the replacement heart valve.

6. The method of claim 1 wherein the intestinal tissue is kept in tubular form throughout all steps of extraction, trimming, and surgical implantation.

7. The method of claim 6 wherein the surgically-implantable segment of intestinal tissue is used to replace an atrioventricular heart valve having at least two leaflets, wherein the first end of the segment of intestinal tissue is secured to an atrioventricular valve annulus, and wherein the second opposing end of the segment of intestinal tissue is trimmed to provide leaflets which are secured to papillary muscles in a manner which generates a valve outlet end.

8. The method of claim 1 wherein the surgically-implantable segment of intestinal tissue is secured inside a stent in a manner which generates a cusp in a semilunar replacement valve.

9. The method of claim 1 wherein the surgically-implantable segment of intestinal tissue is used to replace a semilunar valve inside an arterial wall adjacent to a heart, by steps comprising:

a. securing a first end of the surgically-implantable segment of intestinal tissue to a valve annulus from which native semilunar cusps have been removed;

b. securing a second opposing end of the surgically-implantable segment of intestinal tissue to the arterial wall at three constraint locations positioned approximately equidistantly around the second end of the intestinal tissue, in a manner which creates three intestinal tissue flaps positioned between the three constraint locations, in a manner which allows the three intestinal tissue flaps to flex inwardly, inside the arterial wall adjacent to the heart, and thereby function as semilunar cusps during opening and closure of the semilunar replacement valve.

10. The method of claim 9 wherein the intestinal tissue is extracted from the patient who receives the replacement heart valve.

\* \* \* \* \*